(12) United States Patent
Oraevsky et al.

(10) Patent No.: US 10,123,707 B2
(45) Date of Patent: Nov. 13, 2018

(54) OPTOACOUSTIC IMAGE MAPPING OF TISSUE TEMPERATURE

(71) Applicants: Alexander A. Oraevsky, Houston, TX (US); Elena Petrova, Houston, TX (US); Sergey Ermilov, Houston, TX (US)

(72) Inventors: Alexander A. Oraevsky, Houston, TX (US); Elena Petrova, Houston, TX (US); Sergey Ermilov, Houston, TX (US)

(73) Assignee: TomoWave Laboratories, Inc., Houston, TX (US)

( * ) Notice: Subject to any disclaimer, the term of this patent is extended or adjusted under 35 U.S.C. 154(b) by 620 days.

(21) Appl. No.: 14/611,722

(22) Filed: Feb. 2, 2015

(65) Prior Publication Data

US 2015/0216420 A1 Aug. 6, 2015

Related U.S. Application Data

(60) Provisional application No. 61/934,529, filed on Jan. 31, 2014.

(51) Int. Cl.
*A61B 5/00* (2006.01)
*A61B 5/01* (2006.01)
(Continued)

(52) U.S. Cl.
CPC ............ *A61B 5/0095* (2013.01); *A61B 5/015* (2013.01); *A61B 5/7425* (2013.01); *A61B 8/085* (2013.01);
(Continued)

(58) Field of Classification Search
CPC ....... A61B 5/0095; A61B 5/1459; A61B 8/08; A61B 90/36
See application file for complete search history.

(56) References Cited

U.S. PATENT DOCUMENTS

| 5,840,023 A | 11/1998 | Oraevsky et al. |
| 6,309,352 B1 | 10/2001 | Oraevsky et al. |

(Continued)

OTHER PUBLICATIONS

Junjie Yao, Haixin Ke, Stephen Tai, Yong Zhou, Lihong V. Wang. Absolute Photoacoustic Thermometry in Deep Tissue Opt Lett. 2013. 38: 5228-5231.

(Continued)

*Primary Examiner* — Joel Lamprecht
(74) *Attorney, Agent, or Firm* — Benjamin Aaron Adler

(57) ABSTRACT

Provided herein are system and methods for monitoring and guiding thermal therapy procedures within a human or animal tissue. The system comprises a therapeutic module configured to apply thermal treatment to a subject; an ultrasound imaging module; an optoacoustic imaging module; a processing module connected to both ultrasound and optoacoustic based imaging module; and an operating controlling module connected with said processing module and configured to manipulate at least one of said therapeutic module, ultrasound imaging module or optoacoustic imaging module. The calibration method is able to eliminate the inconsistency of optoacoustic based temperature measurements caused by sample-to-sample and spatial variations of Gruneisen parameter for different tissues. The method for temperature-structure imaging is able to generate both two dimensional and three dimensional co-registered structure and temperature images for the tissues inside a region of interest of a subject.

16 Claims, 17 Drawing Sheets

Figure 1:
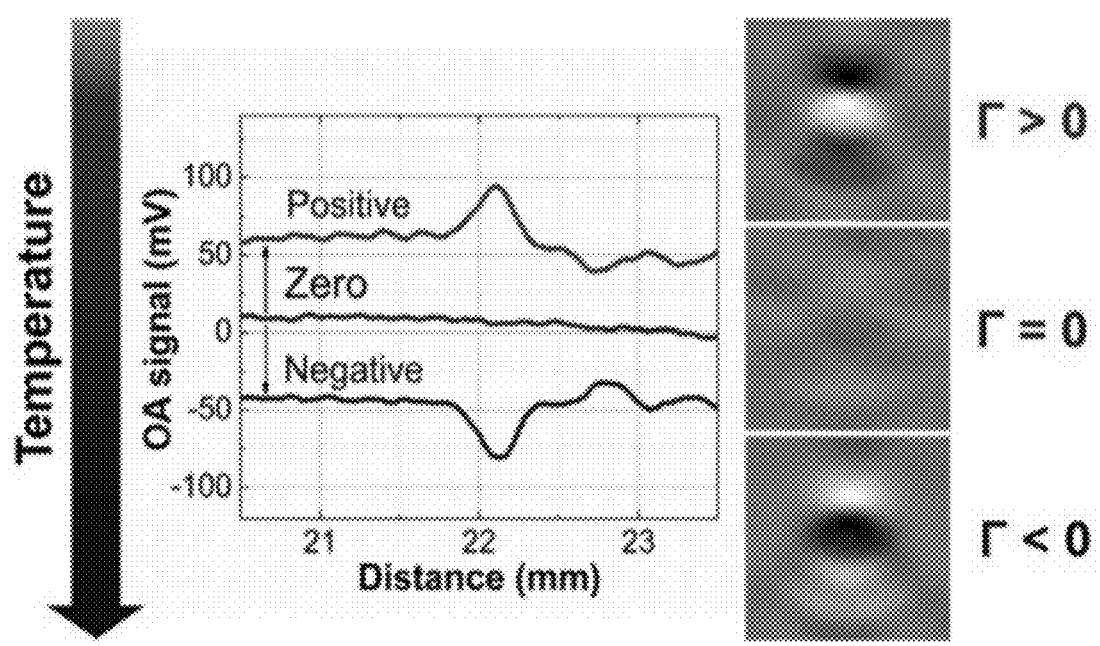

(51) Int. Cl.
  A61B 18/02 (2006.01)
  A61B 8/08 (2006.01)
  A61B 8/14 (2006.01)
  A61B 8/00 (2006.01)
  A61B 18/00 (2006.01)
  A61B 90/00 (2016.01)

(52) U.S. Cl.
  CPC ............ *A61B 8/5207* (2013.01); *A61B 18/02* (2013.01); *A61B 8/14* (2013.01); *A61B 8/463* (2013.01); *A61B 2018/00714* (2013.01); *A61B 2018/0293* (2013.01); *A61B 2090/378* (2016.02); *A61B 2560/0223* (2013.01)

(56) References Cited

U.S. PATENT DOCUMENTS

| | | |
|---|---|---|
| 2005/0085725 A1 | 4/2005 | Nagar et al. |
| 2012/0125107 A1 | 5/2012 | Emelianov et al. |
| 2012/0253180 A1* | 10/2012 | Emelianov ........... A61B 8/0841 600/424 |
| 2013/0096422 A1 | 4/2013 | Boctor et al. |

OTHER PUBLICATIONS

Jignesh Shah, Suhyun Park, Salavat Aglyamov, Timothy Larson, Li Ma, Konstantin Sokolov, Keith Johnston, Thomas Milner, Stanislav Y. Emelianov Photoacoustic imaging and temperature measurement for photothermal cancer therapy. Journal of Biomedical Optics 2008, 13:034024-1 to 034024-9.

Manojit Pramanik, Lihong V. Wang Thermoacoustic and photoacoustic sensing of temperature Journal of Biomedical Optics 2009, 14:054024-1 to 054024-7.

Sergey M. Nikitin, Tatiana D. Khokhlova, Ivan M. Pelivanov Temperature dependence of the optoacoustic transformation efficiency in ex vivo tissues for application in monitoring thermal therapies Journal of Biomedical Optics 2012, 12:061214-1 to 061214-9.

Haixin Ke, Stephen Tai, Lihong V. Wang Photoacoustic thermography of tissue Journal of Biomedical Optics 2014, 19:026003-1 to 0260034.

Da-Kang Yao, Chi Zhang, Konstantin Maslov, Lihong V. Wang Photoacoustic measurement of the Grüneisen parameter of tissue Journal of Biomedical Optics 2014, 19:017007-1 to 017007-7.

Liang Gao, Lidai Wang, Chiye Li, Yan Liu, Haixin Ke, Chi Zhang, Lihong V. Wang Single-cell photoacoustic thermometry, Journal of Biomedical Optics 2013, 18:026003-1 to 026003-5.

Ralf Brinkmann, Stefan Koinzer, Kerstin Schlott, Lars Ptaszynski, Marco Bever, Alexander Baade, Susanne Luft, Yoko Miura, Johann Roider, Reginald Birngruber. Real-time temperature determination during retinal photocoagulation on patients Journal of Biomedical Optics 2012, 17:061219-1 to 061219-10.

Andre Roggan, Moritz Friebel, Klaus Dorschel, Andreas Hahn, Gerhard Muller Optical Properties of Circulating Human Blood in the Wavelength Range 400-2500 nm. Journal of Biomedical Optics 1999 4:36-46.

J. M. Steinke and A. P. Shepherd, Effects of Temperature on Optical Absorbance Spectra of Oxy-, Carboxy-, and Deoxyhemoglobin Clin. Chem. 1992, 38:1360-1364.

Liang Gao, Chi Zhang, Chiye Li, and Lihong V. Wang, Intracellular temperature mapping with fluorescence-assisted photoacoustic-thermometry Applied Physics Letters 2013. 102:193705-1 to 193705-5.

Gunnar Brix, Malte L. Bahner, Ulf Hoffmann, Andrea Horvath, Wolfgang Schreiber, Regional Blood Flow, Capillary Permeability, and Compartmental Volumes: Measurement with Dynamic CT—Initial Experience Radiology 1999; 210:269-276.

Kirill V Larin, Irina V Larina and Rinat O Esenaliev Monitoring of tissue coagulation during thermotherapy using optoacoustic techniqueJ. Phys. D: Appl. Phys.2005. 38:2645-2653.

Elena Petrova,Sergey Ermilov, Richard Su, Vyacheslav Nadvoretskiy, André Conjusteau, and Alexander Oraevsky Using optoacoustic imaging for measuring the temperature dependence of Grüneisen parameter in optically absorbing solutions Opt. Express 2013. 21.25077-25090.

Nykolai Bilaniuk and George S. K. Wong, Speed of sound in pure water as a function of temperature, J. Acoust. Soc. Am. 1993. 93:1609-1612.

Harry H Pennes, Analysis of Tissueand Arterial Bloof Temperatures in the Resting Human Forearm, Journal Applied Physiol. 1948 1:93-120.

M C Koliost, M D Sherarf and J W Huntt, Large blood vessel cooling in heated tissues: a numerical study Phys. Med. Bid. 1995, 40:477-494.

I. Rivens, A. Shaw, J. Civale1, H. Morris, Treatment monitoring and thermometry for therapeutic focused ultrasound Int. J. Hyperthermia, 2007. 23:121-139.

Paola Saccomandi, Emiliano Schena, Sergio Silvestri Techniques for temperature monitoring during laser-induced thermotherapy: An overview, Int J Hyperthermia, 2013; 29: 609-619.

Costas D. Arvanitis, Nathan McDannold Integrated ultrasound and magnetic resonance imaging for simultaneous temperature and cavitation monitoring during focused ultrasound therapies. Med. Phys. 2013: 40:112901-1 to 112901-14.

Rinat O. Esenaliev; Alexander A. Oraevsky; Kirill V. Larin; Irina V. Larina; Massoud Motamedi, Real-time optoacoustic monitoring of temperature in tissues 1999Proceedings SPIE 3601:268-275.

Elena V. Petrova; Sergey A. Ermilov; Richard Su; Vyacheslav Nadvoretskiy; André Conjusteau; Alexander A. Oraevsky, Temperature dependence of Grüneisen parameter in optically absorbing solutions measured by 2D optoacoustic imaging 2014. Proc. SPIE 8943:89430S.

Yun-Sheng Chen, Wolfgang Frey, Salavat Aglyamov, Stanislav Emelianov, Environment-dependent Generation of Photoacoustic Waves from Plasmonic Nanoparticles 2011 Small 8:47 (2012) DOI: 10.1002/smll.201101140.

Chen YS , Frey W, Walker C, Aglyamov S, Emelianov S., Sensitivity enhanced nanothermal sensors for photoacoustic temperature mapping. 2013 J Biophotonics. (6-7):534-42. doi: 10.1002/jbio. 201200219. Epub Mar. 1, 2013.

Cordone L, Cupane A, Leone M, Vitrano E., Optical absorption spectra of deoxy- and oxyhemoglobin in the temperature range 300-20 K. Relation with protein dynamics. 1986 Biophys Chem. 24(3) : 259-75.

* cited by examiner

OPTOACOUSTIC IMAGE MAPPING OF TISSUE TEMPERATURE

CROSS-REFERENCE TO RELATED APPLICATIONS

This non-provisional application claims benefit of priority of provisional application U.S. Ser. No. 61/934,529, filed Jan. 31, 2014, the entirety of which is hereby incorporated by reference.

BACKGROUND OF THE INVENTION

Field of the Invention

The present invention generally relates to the fields of biomedical optoacoustic imaging. Particularly, the present invention relates to real-time imaging systems that visualize maps of temperature in a human or animal body noninvasively and provide independent images of tissue anatomy co-registered with images of temperature variations.

Description of the Related Art

Many in the filed of biomedical science have recognized that accurate noninvasive temperature mapping in vivo in the depth of human (animal) body could lead to ground breaking advances in the thermal therapy and cryotherapy. Hence, in the past few decades, significant efforts have been made to create a device that could achieve this goal.

Optoacoustic imaging and sensing represent a novel biomedical monitoring technologies with contrast based on optical absorption in tissues. Previously, sensing of optoacoustic signals has been proposed for monitoring tissue properties and temperature. It is known that the magnitude of optoacoustic response is sensitive to the local temperature. The phenomenon is attributed to temperature dependent behavior of thermodynamic and mechanical properties, which comprise thermoacoustic efficiency of the tissue, also known as Gruneisen parameter. The presence of temperature dependent optoacoustic response (ThOR) measured as signals generated by laser pulses in biological tissues provided the foundation for non-invasive temperature monitoring. However, currently, when considering in vivo applications of optoacoustic sensing, sample-to-sample and spatial variations of Gruneisen parameter for different tissues remains as the major issue. In other words, under currently technology of optoacoustic imaging, each calibration method only remains valid if the temperature measurement is conducted in the same particular tissue. Therefore, when a population of live biological subjects was studied with prior optoacoustic-based methods, it becomes obvious that the measured temperature accuracy is far from ideal.

Furthermore, current optoacoustic imaging technology only provides the temperature information. To obtain more comprehensive information of a patient, which could allow a medical professional to identify the exact temperature in a particular anatomical locations of interest, a combined image of anatomical structures with corresponding temperatures are highly desirable. It would substantially increase the efficiency of thermal (and cryo) therapy by directly monitoring the treatment of abnormal human tissues and ensuring the safety for surrounding normal tissues. So far, there is no technology that could achieve such an objective.

Thus, there is a recognized need in the art for improved devices and methods for accurate noninvasive temperature mapping, and preferably providing images of anatomical structures co-registered with corresponding temperatures. Particularly, the prior art is deficient in these aspects. The present invention fulfills this longstanding need and desire in the art.

SUMMARY OF THE INVENTION

The present invention is directed to an imaging system for visualization and accurate mapping of temperature in absolute values in the region of interest of live human or animal tissue independently on spatial distribution of the optical fluence in the body and independently on spatial distribution of the tissue optical properties. The imaging system comprises an optoacoustic imaging module that uses pulsed optical illumination at preferred wavelength around 800 nm or around 1300 nm, an image processing and calibration module connected to the optoacoustic imaging module and an operating and controlling module electronically connected with said image processing module and configured to control and manipulate all components of the imaging system. The present invention is directed to another imaging system further comprising an ultrasound imaging module having an ultrasonic probe communicably connected to an electronics system that also serves as a probe and to an electronics system for the optoacoustic imaging module.

The present invention also is directed to an imaging system for monitoring and guiding thermal therapy procedures within a human or animal tissue. The system comprises the imaging system for visualization and accurate mapping of temperature in absolute values as described herein, a therapeutic module configured to apply thermal treatment to a subject and an operating controlling module connected with said processing module and configured to manipulate at least one of said therapeutic module, ultrasound imaging module or optoacoustic imaging module.

The present invention is directed further to a user-implemented method for calibrating a temperature-structure imaging system. The method comprises the steps of (a) illuminating a tissue with the laser pulses of the optoacoustic imaging module of claim 1 and acquiring optoacoustic signals from the illuminated tissue to generate a first optoacoustic image at human physiological temperature; (b) applying an automatic self-focusing algorithm in the image processing module to determine the temperature dependent speed of sound in a region of interest of a patient's body and obtain the optimal resolution for the first optoacoustic image and (c) turning on the temperature cooling source and allow time for the temperature of region of interest to change and create gradient of the spatial distribution of temperature, T(r). Step (d) applies step (a) at a changed temperature and a second optoacoustic image is acquired. Step (e) applies step (b) and optimizes resolution of the second optoacoustic Image to achieve matching between localization of tissue structures in the first image and the second optoacoustic image. Step f) normalizes the second optoacoustic image to the first optoacoustic image by dividing every pixel of the second optoacoustic image intensity to that of corresponding pixel of the first optoacoustic image, and thereby produce a normalized image of the optoacoustic image intensity ratio proportional to temperature ratio. In step (g) temperature is measured with thermocouples placed in the region of interest along temperature gradient to calibrate the map generated in step (g) in absolute temperature value. In Step (h) steps (d) through (g) are repeated to acquire a sequence of optoacoustic images and display of temperature distribution maps, which undergoes changes in the course of calibration procedure and, in step (i), calibration curve data is recorded from images of spatial distribution of the temperature in the calibration tissues or phantoms that resemble properties of the region of interest in the human body;

The present invention is also directed to a method for mapping the temperature of a tissue in the course of thermal therapy procedure. The method comprises in step (a) illuminating a tissue inside a region of interest of a subject using laser pulses of the optoacoustic imaging module as described herein at a wavelength within preferred spectral range and safe optical fluence and in step (b) measuring an optoacoustic response of the tissue by using the ultrasonic probe. In step (c) constructing a first optoacoustic image at a physiological temperature inside said subject. In step (d) an automatic self-focusing algorithm is applied for the first optoacoustic image to determine the temperature dependent speed of sound in the region of interest of a subject and achieve an optimal resolution for the first optoacoustic image. In step (e) a spatial distribution for temperature in the subject is created by performing thermal therapy on the subject. In step (f) the tissue is illuminated in the same region of interest at the second temperature point, in the same position of the subject, using laser pulses at the same preferred laser wavelength and the same optical fluence and in step (g) a second optoacoustic image at the second temperature is constructed. In step (h) the automatic self-focusing algorithm is applied for the second optoacoustic image to determine the temperature dependent speed of sound in the region of interest of a subject and achieve an optimal resolution for the second optoacoustic image at the second temperature. In step (i) a normalized image of the optoacoustic image intensity ratio is generated by dividing every pixel value of the second optoacoustic image to corresponding pixel value on the first optoacoustic image and in step (j) calibrating the normalized optoacoustic image is calibrated using the calibration curve described herein. In step (k) a map of temperature distribution on the tissues inside the region of interest of the subject is produced. In step (l) steps f) to step k) are repeated for generating a map of absolute temperature distribution in real time and in step (m) the map of the temperature distribution inside the region of interest of the subject issued to guide the thermal therapy procedure.

BRIEF DESCRIPTIONS OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

FIG. 1 demonstrates how optoacoustic signals and images change in the process of temperature decreasing from physiological temperature to the temperature zone where the optoacoustic response is zero in the blood of a subject.

Figure 2:
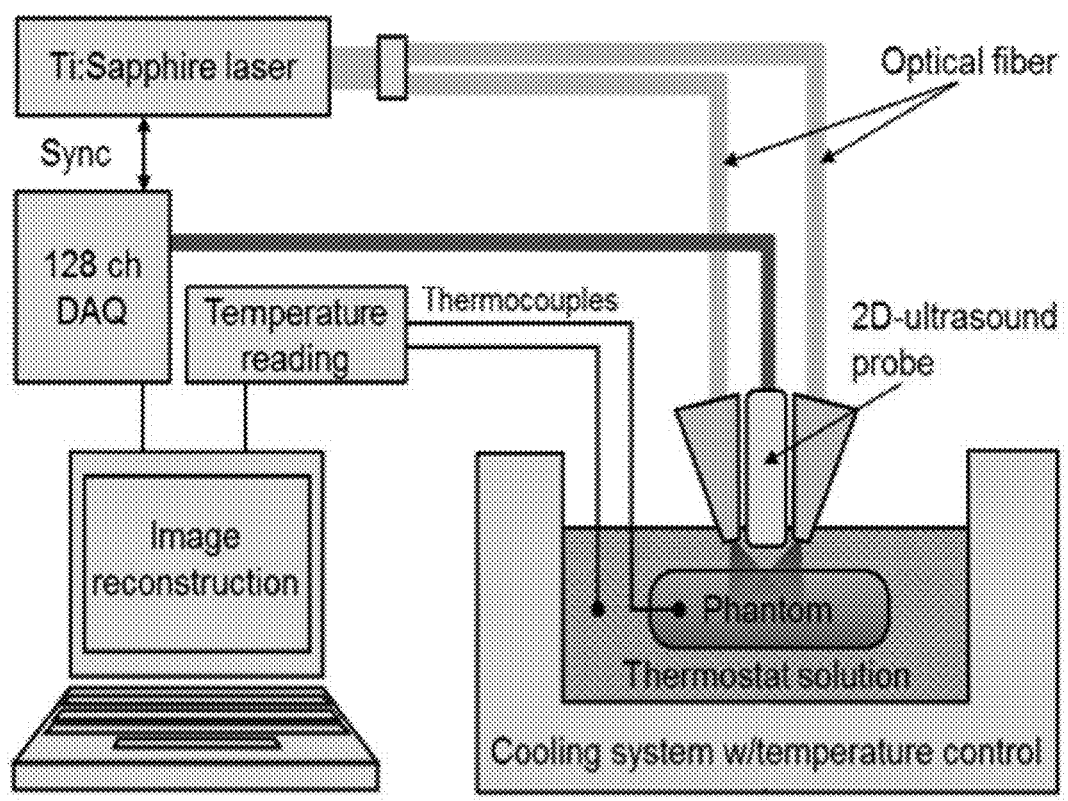

FIG. 2 demonstrates experimental block diagram of the calibration system of the present invention as applied to laboratory calibration procedure using phantoms.

Figure 3A:
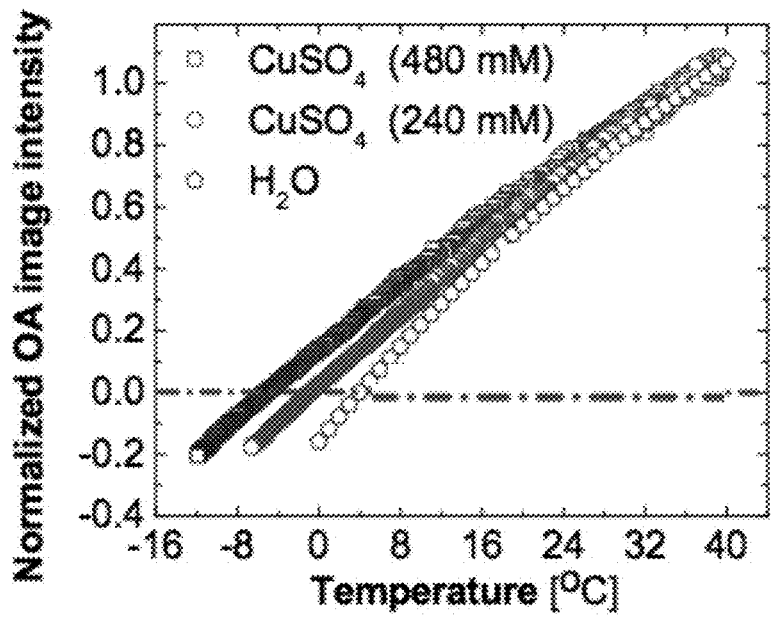
Figure 3B:
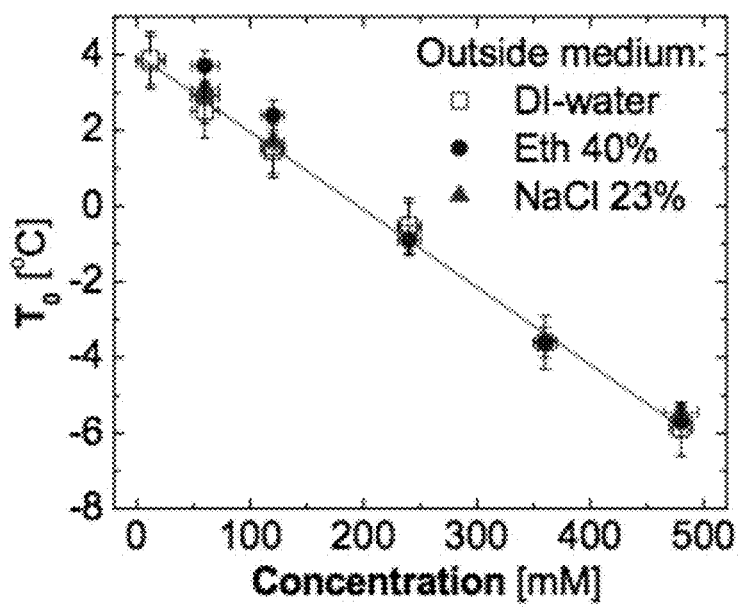
Figure 3C:
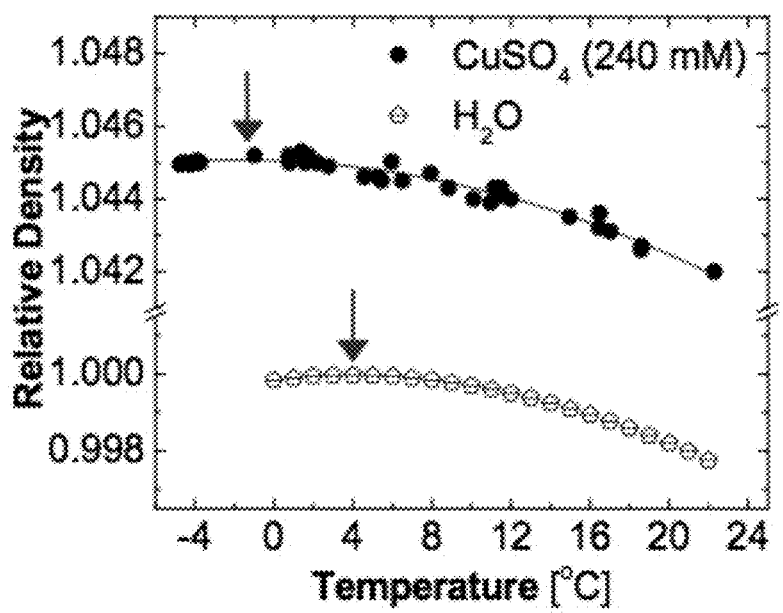
Figure 3D:
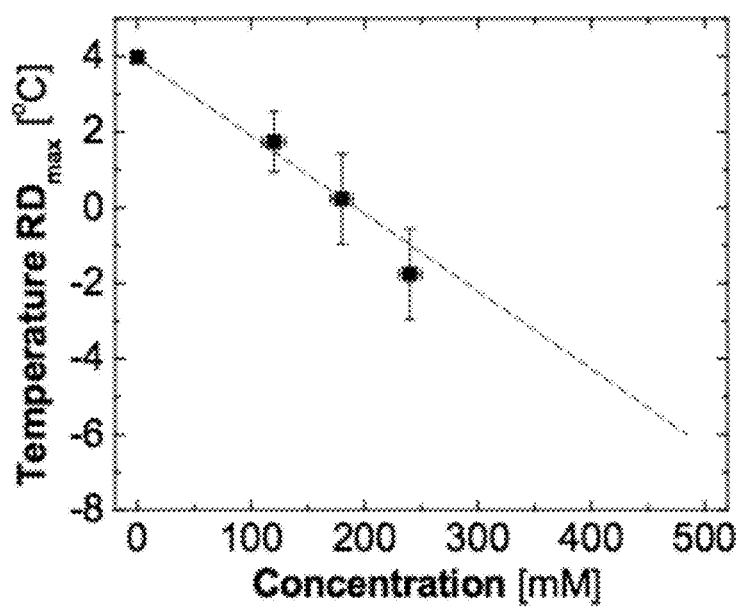

FIGS. 3A-3D illustrate the temperature dependence of optoacoustic image intensity in a region of interest for aqueous solution of $CuSO_4.5H_2O$ and calculated Gruneisen parameter for water after normalization at 37° C. (FIG. 3A); the concentration dependence of T° C., at which thermal condition dependent optoacoustic response of tissue is equal to zero (FIG. 3B); temperature dependence of relative density for aqueous solution of $CuSO_4.5H_2O$ (240 mM) with the second order polynomial regression (FIG. 3C); temperature of maximum relative density as a function of $CuSO_4.5H_2O$ concentration (FIG. 3D).

Figure 4A:
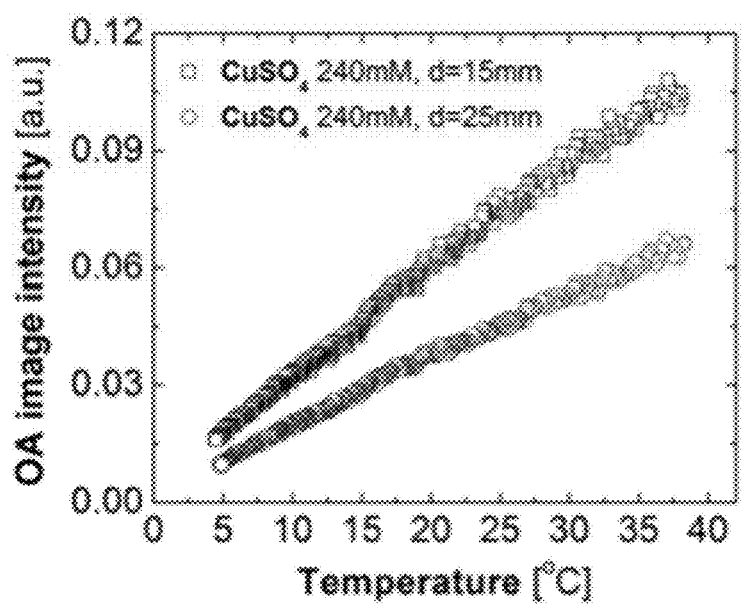
Figure 4B:
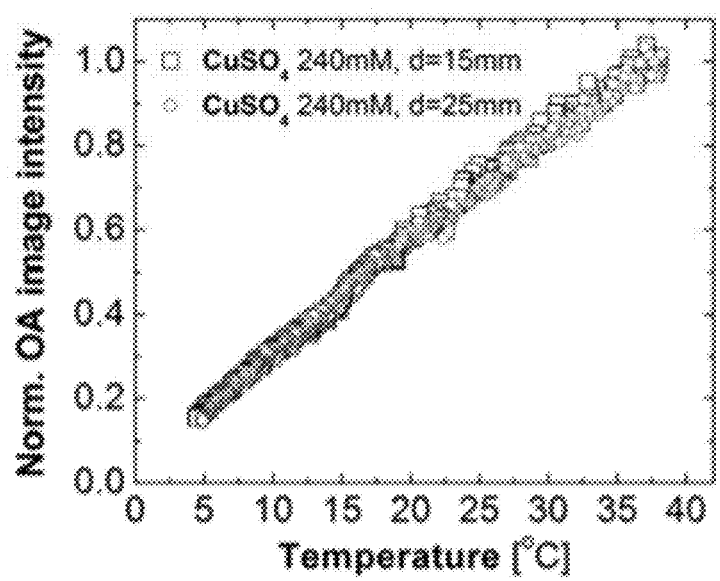

FIGS. 4A-4B demonstrate results from image data matching experiments conducted using two tubes filled with the same solution but placed at different distances between the light emitting fiber bundles and the ultrasonic probe. FIG. 4A illustrates temperature dependence of optoacoustic image intensity in a region of interest for the two tubes. FIG. 4B demonstrates that optoacoustic image intensity of every pixel normalized to that at 37° C. leads to complete match of data for both tubes. Time interval between image recordings was about 30 seconds. The total duration of the cooling procedure was about 180 minutes.

Figure 5A:
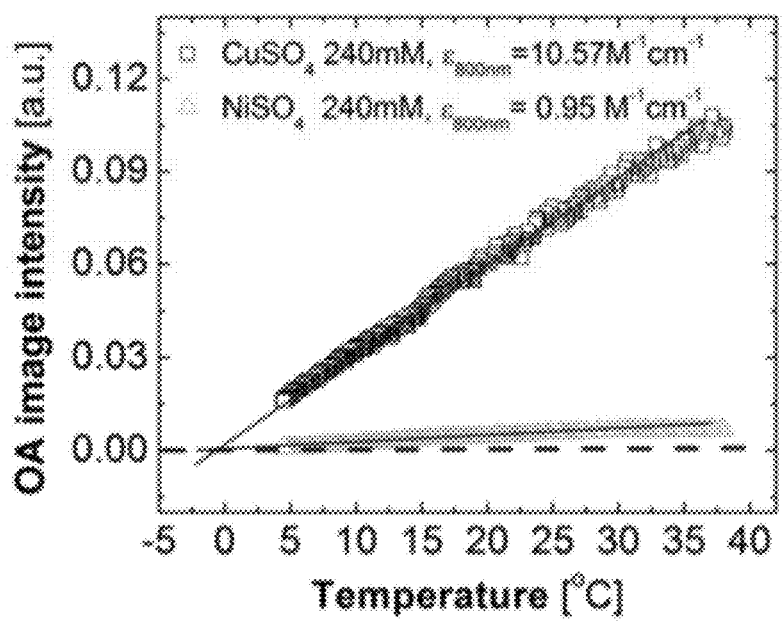
Figure 5B:
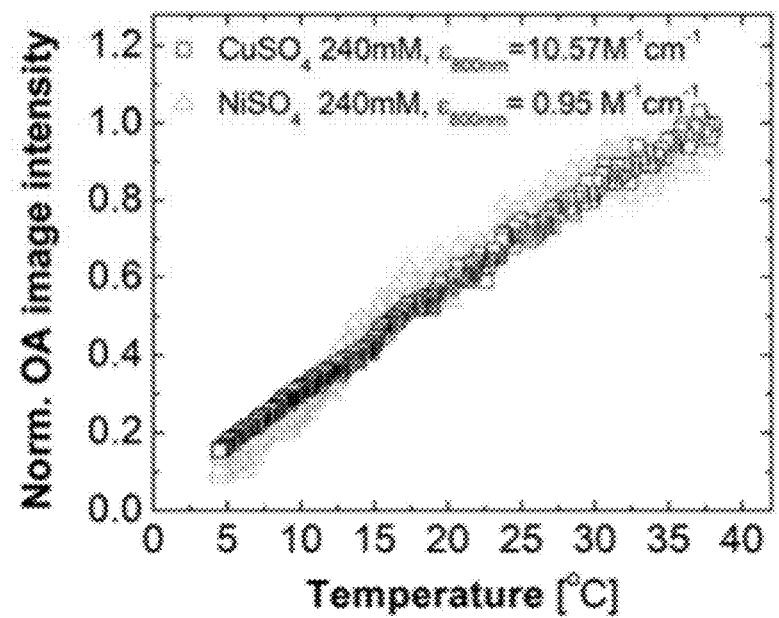

FIGS. 5A-5B depict optoacoustic image intensity as a function of temperature measured from the nickel sulfate and cupric sulfate solutions with the same molar concentrations (FIG. 5A); optoacoustic image intensity data measured at gradually changing temperature normalized to the OA image of each pixel intensity measured at 37° C. (FIG. 5B).

Figure 6A:
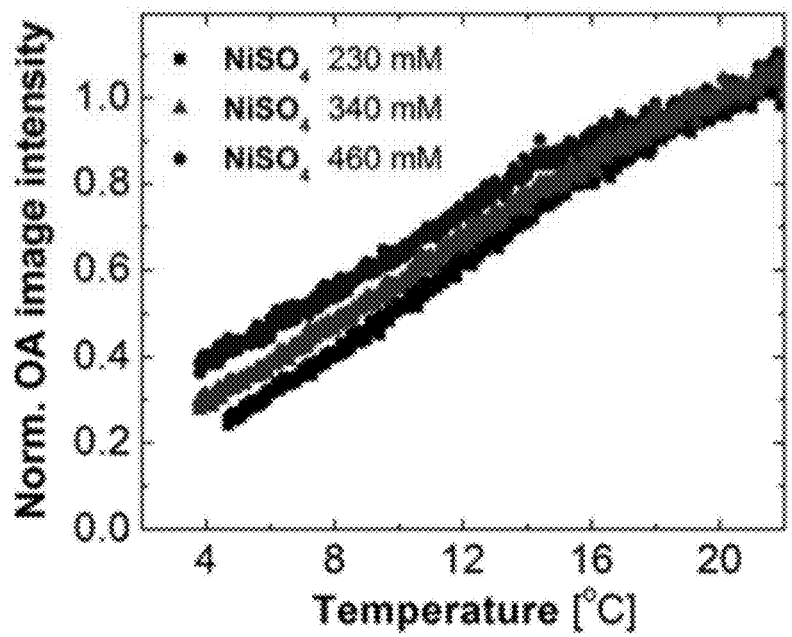
Figure 6B:
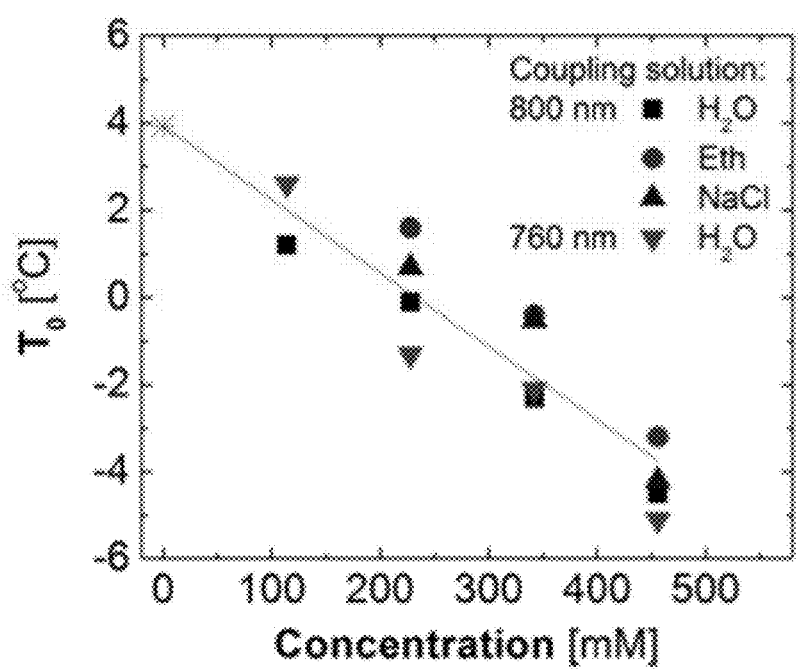

FIGS. 6A-6B show temperature dependence of the optoacoustic image intensity normalized at 20° C. for nickel sulfate solution at different concentrations with water as an acoustically coupling liquid (FIG. 6A); temperature of zero thermal conditions dependent optoacoustic response of tissue as a function of solution concentration measured for NiSO4 solution in different optoacoustic coupling media and its linear fit. This graph demonstrates that the temperature of zero thermal conditions dependent optoacoustic response of tissue is independent on optoacoustic coupling media (FIG. 6B).

Figure 7:
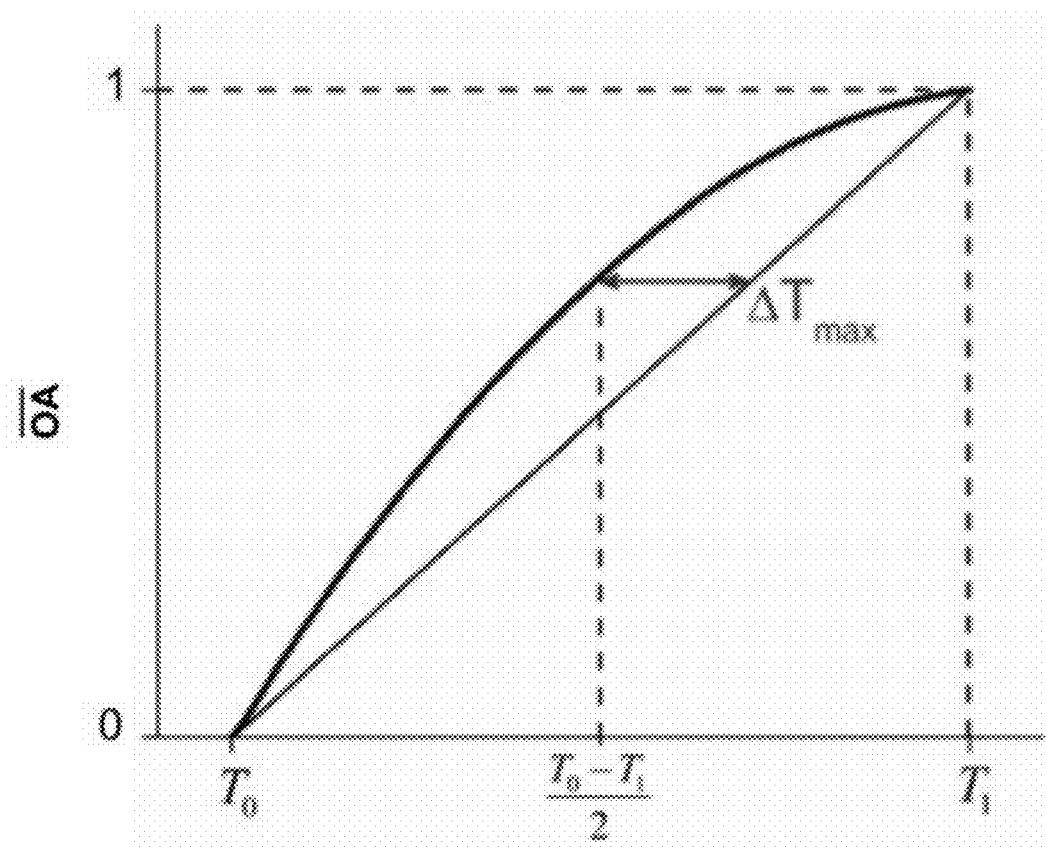

FIG. 7 illustrates that optoacoustic imaging intensity is a nonlinear function of temperature, but it may be approximated with a linear function with sufficient accuracy. The range of temperature monitoring is mathematically determined with the value of maximum nonlinear temperature deviation $\Delta T_{max}$.

Figure 8A:
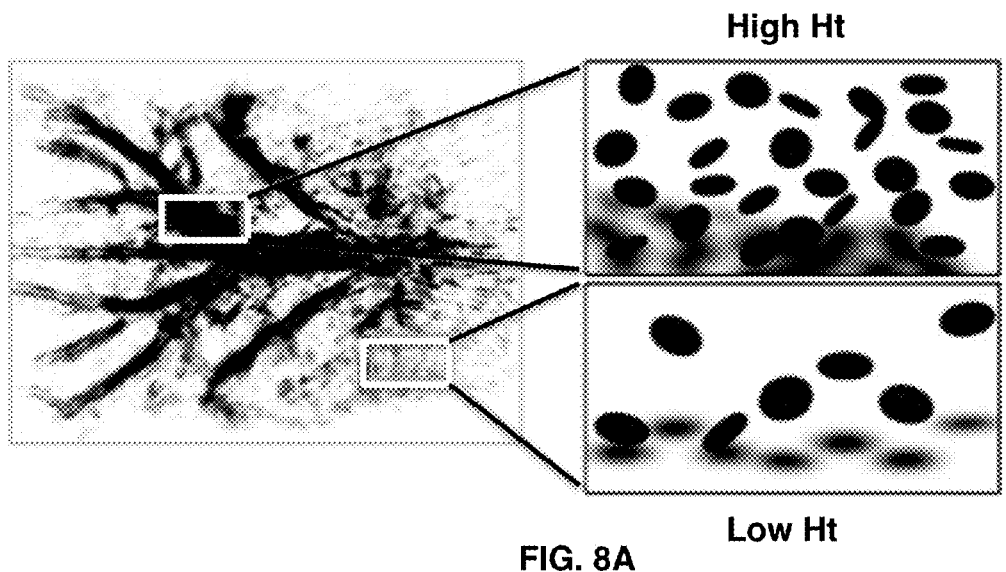
Figure 8B:
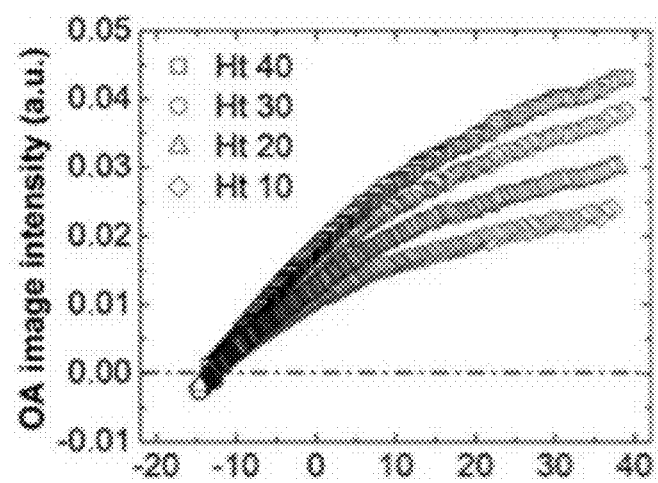
Figure 8C:
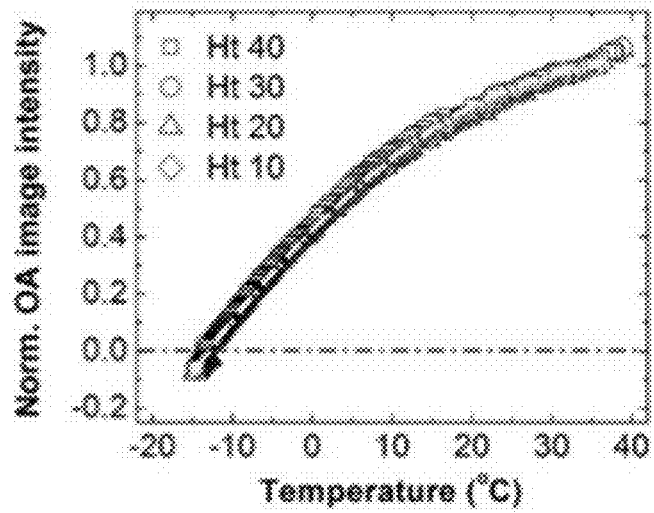

FIGS. 8A-8C illustrate that volumetric fraction of erythrocytes (hematocrit, Ht) significantly varies through the entire vascular network, decreasing from systemic blood vessels down to capillaries (FIG. 8A); experiments with whole and diluted blood demonstrating that the optoacoustic temperature dependent response (ThOR) is scaled proportionally to hematocrit (FIG. 8B); when normalized at 37° C., the thermal conditions dependent optoacoustic response of tissue becomes invariant as the curves representing whole and diluted blood coincide (FIG. 8C).

Figure 9A:
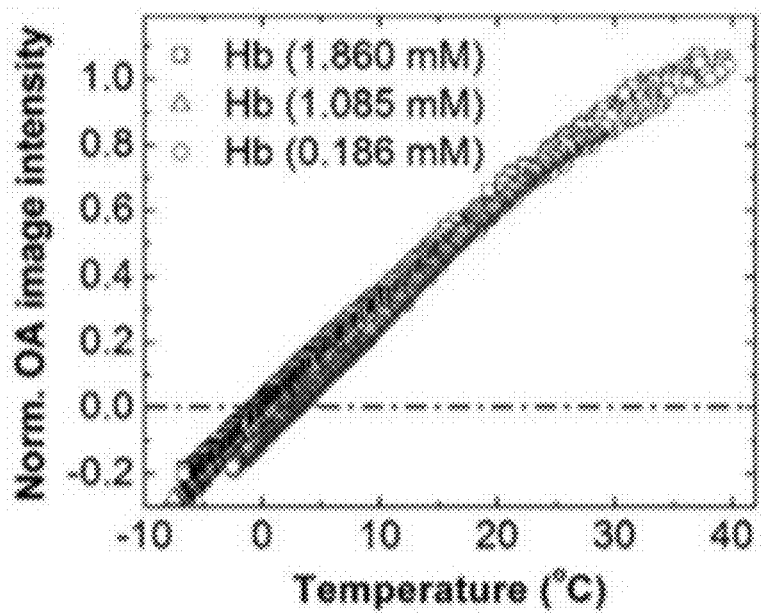
Figure 9B:
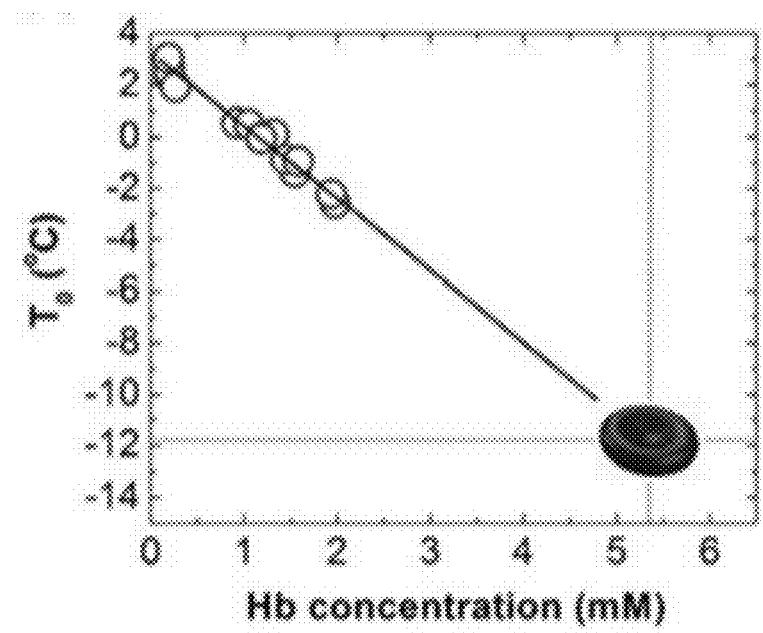

FIG. 9A-9B show optoacoustic image intensity normalized at 37° C. as a function of temperature for three different concentrations of hemoglobin. Dash dotted line marks zero optoacoustic response (FIG. 9A) and temperature $T_0$ of zero thermal conditions dependent optoacoustic response of tissue as a function of hemoglobin concentration (FIG. 9B).

Figure 10A:
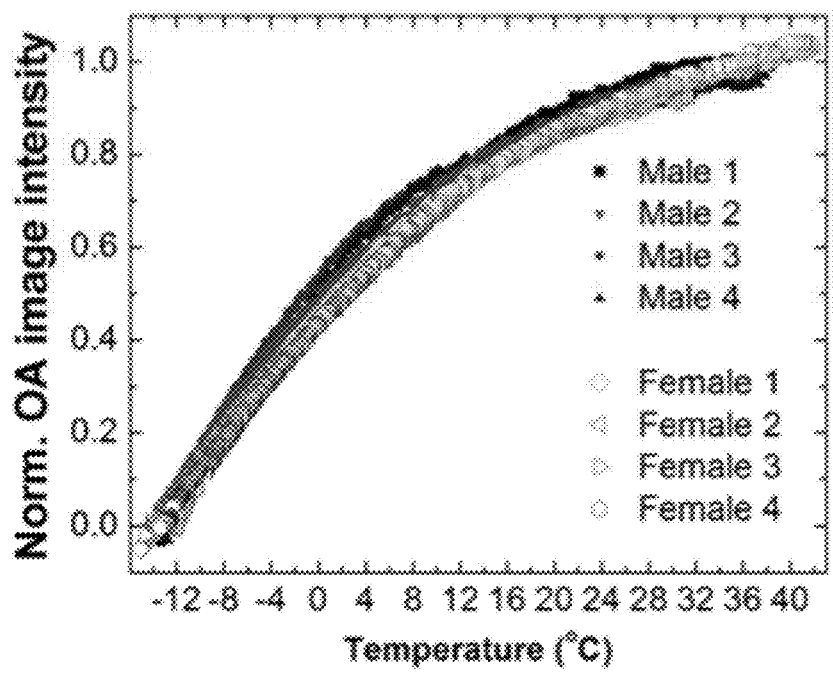
Figure 10B:
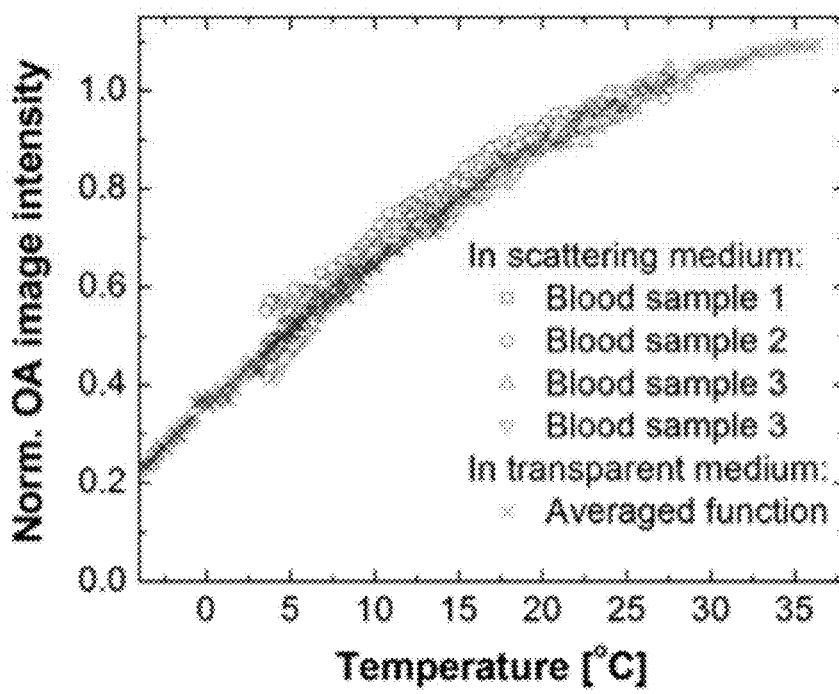

FIG. 10A-10B depict ThOR in porcine blood samples collected from eight animals (4 males and 4 females). At least three tubes positioned at different distances from the probe were filled with each blood sample. Measured optoacoustic response data were averaged over different tubes (FIG. 10A) and the thermal conditions dependent optoacoustic response of tissue of blood in scattering medium in comparison to that in transparent medium. optoacoustic image intensity normalized at 27° C. (FIG. 10B).

Figure 11A:
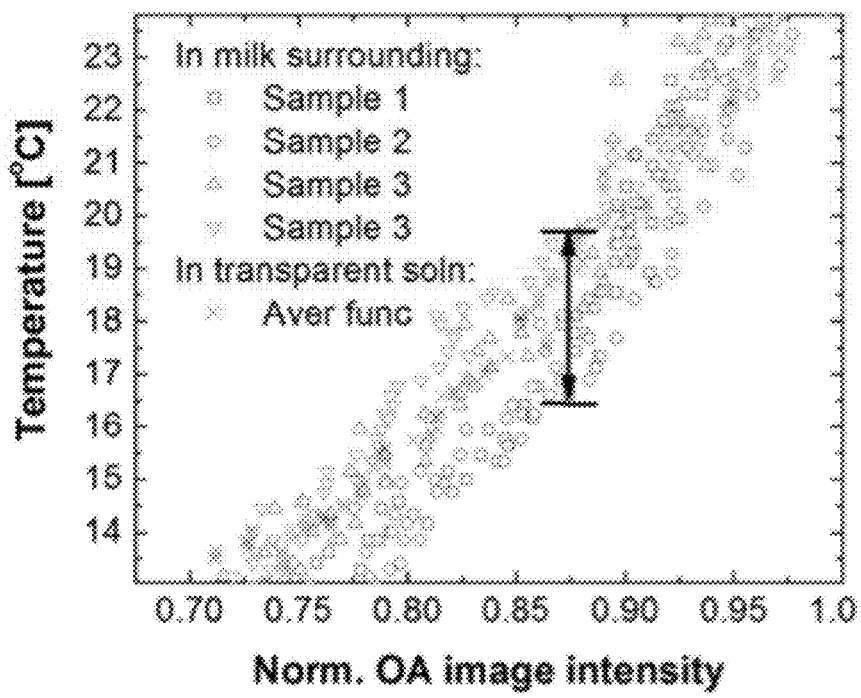
Figure 11B:
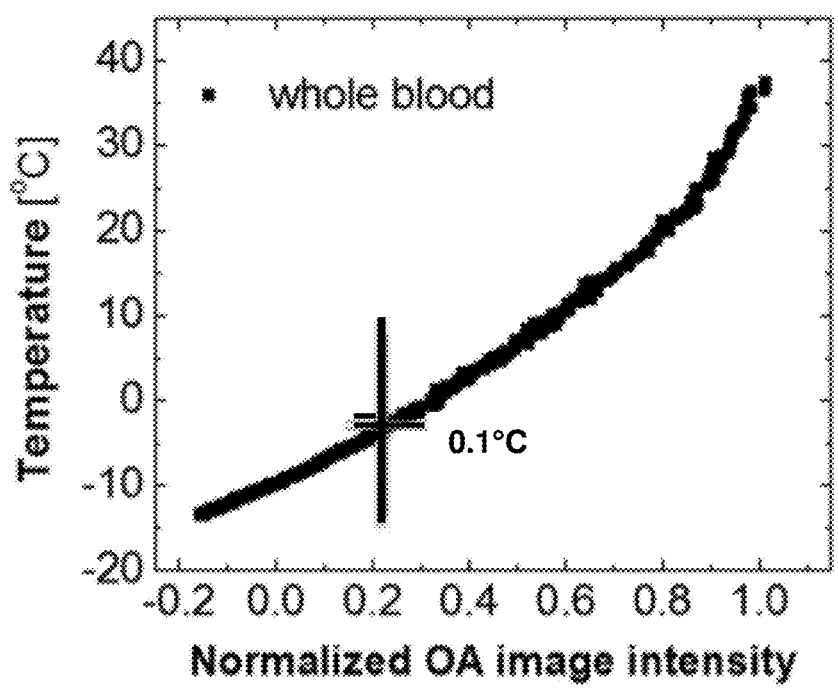

FIG. 11A-11B show zoomed in temperature-dependent optoacoustic response of blood in scattering medium comparing to averaged ThOR function in transparent surrounding. OA image intensity normalized at 27° C. Accuracy of an individual temperature reading in milk surrounding is ±1.5° C. (FIG. 11A); and the temperature monitoring function T of normalized optoacoustic image intensity at 37° C. for whole pigs blood is presented after median filtration and characterized by polynomial fit of second order (FIG. 11B).

Figure 12A:
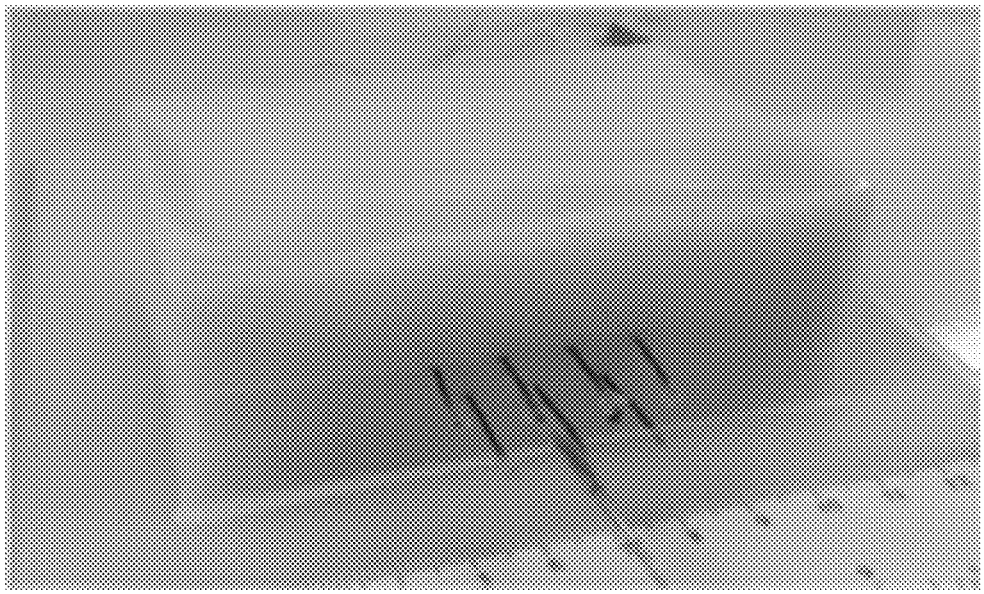
Figure 12B:
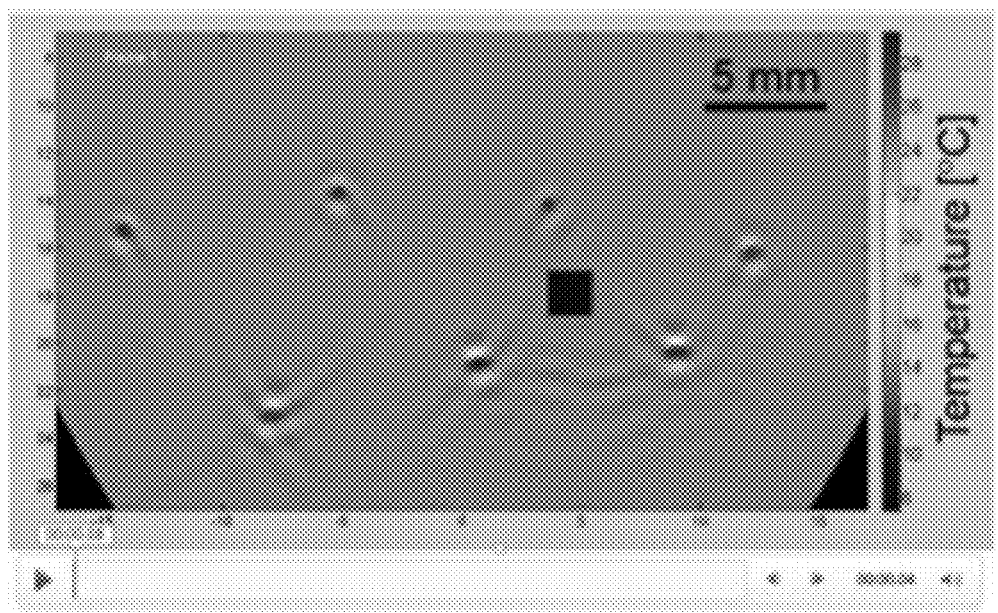
Figure 12C:
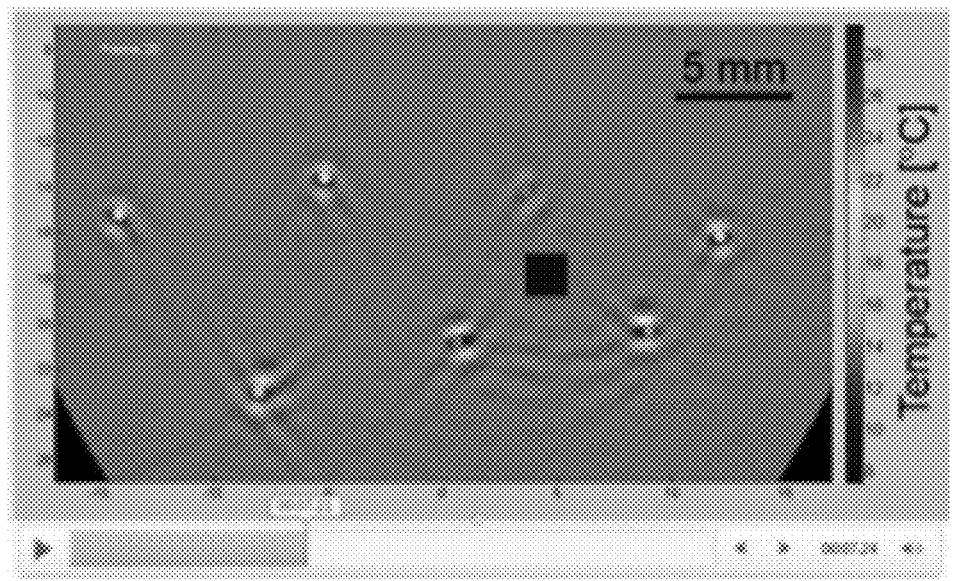
Figure 12D:
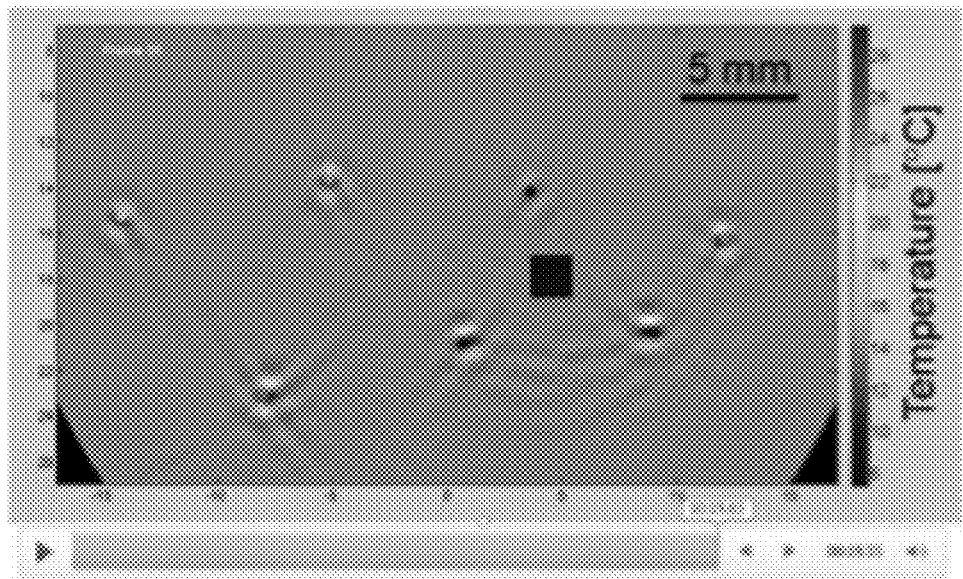

FIGS. 12A-12D show photographs of tissue-mimicking optoacoustic phantom (optically scattering PVCP background and seven tubes Ø0.635 mm filled with live blood) preheated to 36.5° C. (left upper) (FIG. 12A). FIGS. 12B-12D show 3 sample frames of a movie recorded with video rate. The frames present temperature images of tube cross-sections (circles) changing their intensity converted into color from red (FIG. 12B) to yellow (FIG. 12C) to blue (FIG. 12D) depending on gradually decreasing local temperature (° C.) mapped using the method of the present invention. A square on images represent a tube filled with cold water at −11° C. (refrigerated NaCl solution was circulated in the tube).

Figure 13:
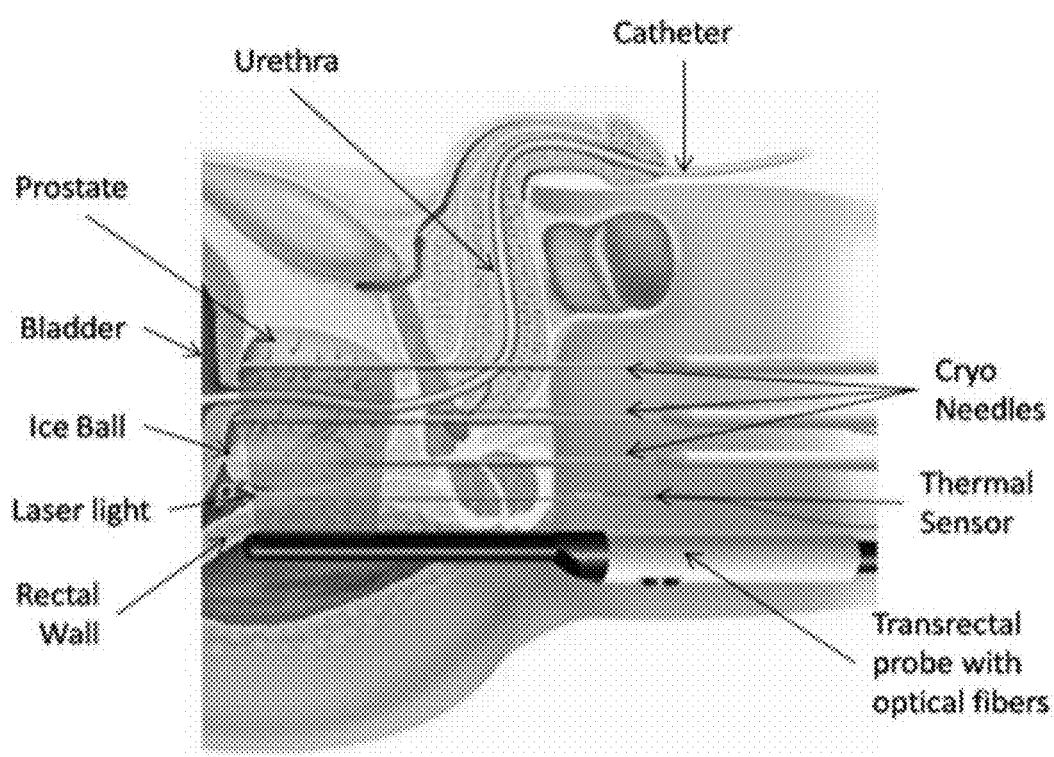

FIG. 13 depicts a clinical cryoablation procedure with optoacoustic temperature monitoring. Ultrasound imaging shows anatomy of region of interest and allows precise insertion of cryoablation needles. Transrectal ultrasonic probe is designed to include fiberoptic bundles for optical illumination with NIR laser pulses. Deep penetration of NIR light at preferred wavelengths through the scattering medium allows non-invasive temperature monitoring with clinical significance.

Figure 14A:
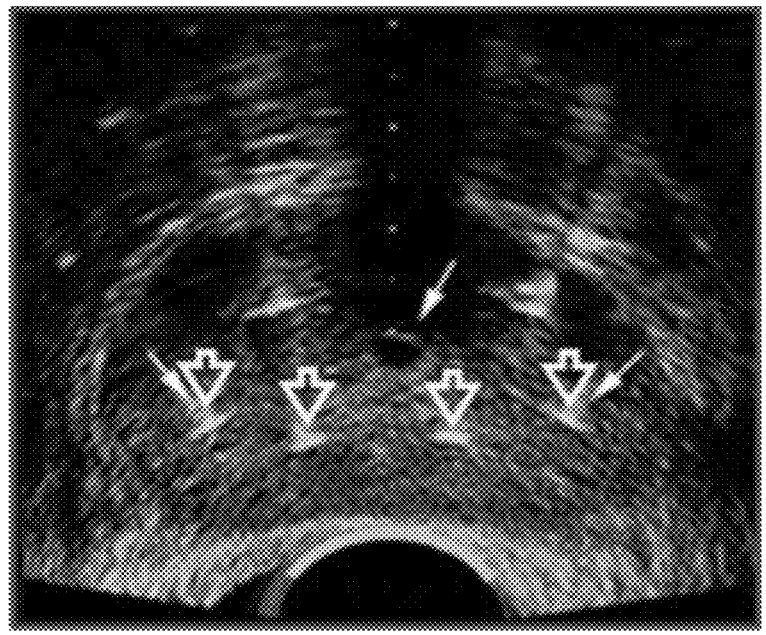
Figure 14B:
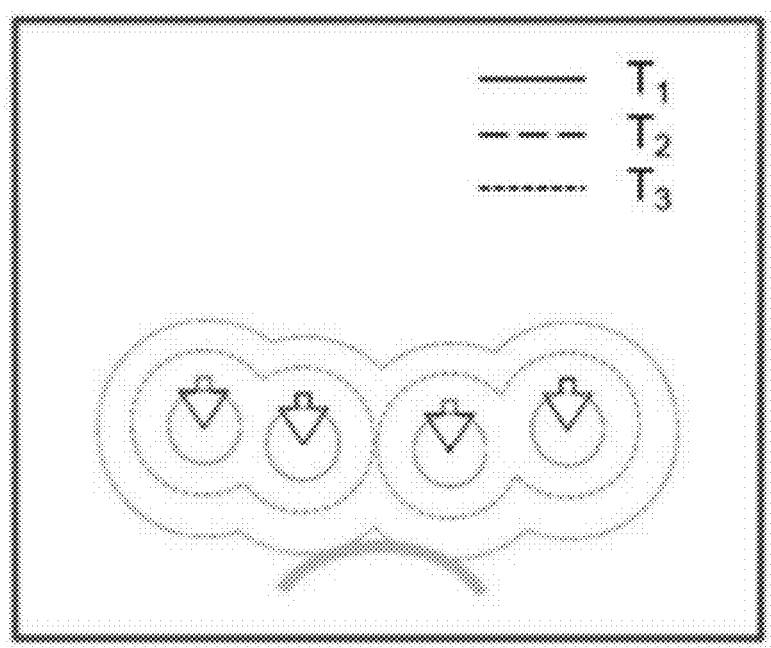
Figure 14C:
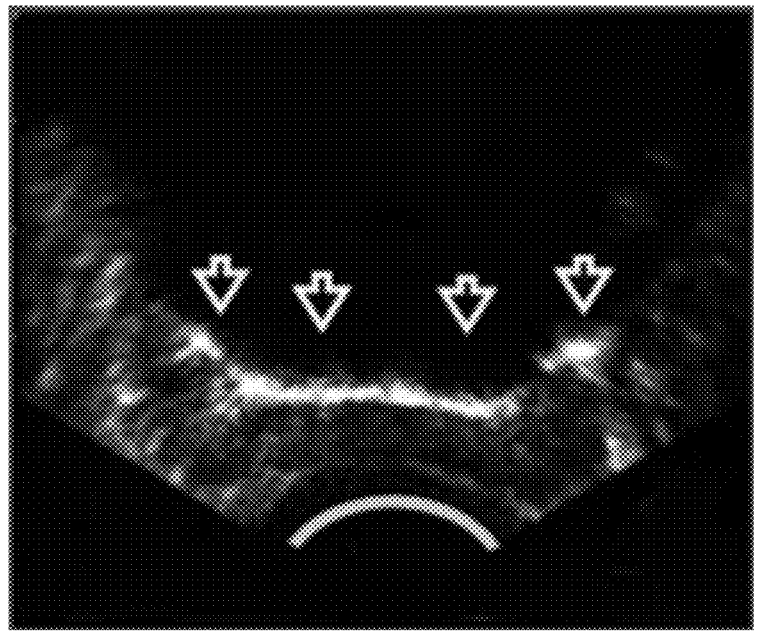
Figure 14D:
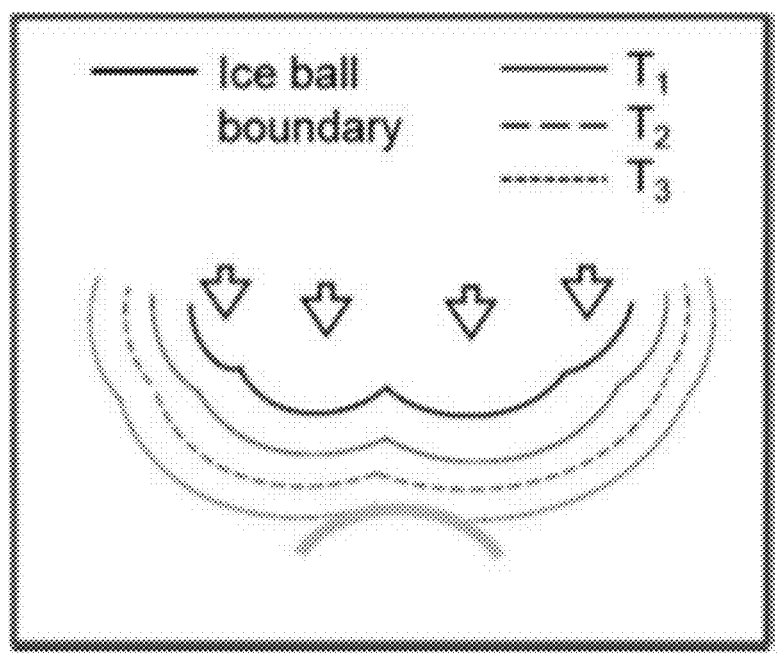

FIGS. 14A-14D depict temperature monitoring during clinical image-guided cryoablation of prostate cancer. FIG. 14A shows ultrasound image of the prostate with inserted 4 cryo-needles. Arrows point to the locations of cryogenic needles, the small arrow shows urethra, which is being kept warm with a warm liquid. The arc at the bottom indicates position of the rectal wall. FIG. 14B shows coalesced ice-balls created around the cryo-needles and visible at bottom as a crescent-shaped line. Sharp change of the normalized optoacoustic image intensity also permits tracking of the ice-ball boundary with real-time optoacoustic image as shown in FIG. 14C. FIG. 14D shows a contour map of isotherms revealing distribution of temperature generated with a system of the present invention.

DETAILED DESCRIPTION OF THE INVENTION

As used herein, the following terms and phrases shall have the meanings set forth below. Unless defined otherwise, all technical and scientific terms used herein have the same meaning as commonly understood to one of ordinary skill in the art.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof. The terms "comprise" and "comprising" are used in the inclusive, open sense, meaning that additional elements may be included.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the term "computer" or "computer system" refer to one or more machines that comprise at least a memory, a processor, a display, one or more interfaces and at least one wired and/or wireless network connection. A computer may be a desktop or laptop machine or other electronic media, for example, a smartphone or tablet, as are standard and currently known in the art. As such computer may comprise a user input device such as a keyboard, keypad, touch screen, mouse, trackball, camera, microphone, and/or other like user input device. Without being limiting, any software, modules, applications, add-ons, plug-ins, programs and/or databases, etc. and associated instructions and/or functions necessary for implementation of any imaging system or dual modality imaging system or subsystems or means comprising the same may be programmed into the computer, may be retrieved over the network connection or may be retrieved from a non-transitory machine-readable media, such as computer readable media or storage device tangibly storing the same, may be tangibly stored in computer memory or other electronic media memory and are executable by the processor comprising the computer.

As used herein, the term "subject" refers to an animal or human, particularly a patient.

As used herein, the term "ThOR" refers to Thermal conditions dependent Optoacoustic Response of tissue, i.e. optically induced temperature dependent pressure wave propagating as ultrasound.

As used herein, the term "ROI" refers to a region of interest within biological tissue in which temperature distribution is being monitored As used herein, the term "Preferred Wavelength" refers to the laser illumination wavelength at which the optical absorption coefficient of the dominating tissue chromophore is constant and independent on changing tissue properties. For hemoglobin of blood as the dominating tissue chromophore the preferred wavelength is selected at which the optical absorption is independent on blood oxygenation and temperature. For cases of water being the dominating tissue chromophore, the optical absorption coefficient must be stronger than that of other tissue constituents and independent on temperature. A contrast agent can be used as a dominating exogenous chromophore.

As used herein, the term Dominating Chromophore refers to a molecule or substance with such a strong optical absorption, so that optical absorption of all other tissue chromophores can be neglected As used herein, the term "Ultrasonic Probe" refers to an array of ultrasonic transducers capable of properly detecting optoacoustic signals As used herein, the term "SoS" refers to the speed of sound As used herein, the term "Optoacoustic Image" refers to the image that displays pixel intensity value as the product of Gruneisen parameter, optical absorption coefficient and optical fluence.

As used herein, the term "Normalized Optoacoustic Image" refers to the image that displays ratio of pixel intensity at unknown temperature to the pixel intensity at a well-known temperature. This ratio image is independent on the distributions of the optical absorption and the optical fluence, and thus, can be calibrated in values (units) of temperature.

As used herein, the term "PVCP" refers to the poly(vinyl chloride) plastisol, a tissue phantom material.

In one embodiment of the present invention, there is provided an imaging system for visualization and accurate mapping of temperature in absolute values in the region of interest of live human or animal tissue independently on spatial distribution of the optical fluence in the body and independently on spatial distribution of the tissue optical properties, comprising an optoacoustic imaging module that uses pulsed optical illumination at preferred wavelength around 800 nm or around 1300 nm; an image processing and calibration module connected to the optoacoustic imaging module; and an operating and controlling module electronically connected with said image processing module and configured to control and manipulate all components of the imaging system. Further to this embodiment the imaging system comprises an ultrasound imaging module having an ultrasonic probe communicably connected to an electronics system that also serves as a probe and to an electronics system for the optoacoustic imaging module.

In another embodiment of the present invention, there is provided an imaging system for visualization of tissue anatomical structures and mapping of temperature distribution within a region of interest in human or animal tissue, comprising the optoacoustic imaging and temperature mapping system as described supra; an ultrasound imaging module for imaging tissue anatomical structures; an image processing module connected to both ultrasound and optoacoustic imaging module; and an image display module programmed to display either image of anatomical structure or temperature or both. In this embodiment, the system is configured to generate two types of images, temperature and anatomical structure, coregistered in space and time for the same tissues in a patient's body.

In this embodiment the optoacoustic imaging module may integrate a pulsed laser connected with an imaging module through a light delivery subsystem configured to deliver the laser pulses to the region of interest. Also in this embodiment the system may be configured to generate two types of images that are temperature and anatomical structure images which are coregistered in space and time for the same tissues in a patient's body.

In yet another embodiment of the present invention, there is provided an imaging system for monitoring and guiding thermal therapy procedures within a human or animal tissue, comprising the imaging system for visualization of tissue anatomical structures and mapping of temperature distribution within a region of interest in human or animal tissue as described supra; a therapeutic module configured to apply thermal treatment to a subject; and an operating controlling module connected with said processing module and configured to manipulate at least one of the therapeutic module, ultrasound imaging module or optoacoustic imaging module.

In this embodiment the processing module may comprise a calculation module configured to calculate the location and temperature within specific anatomical tissue structures based on the information received in the processing module; an image constructing module that generate images based on the calculation from the calculation module and the signals received in the processing module; and an user interface communicably connected to said calculation module, said image constructing module. Particularly, the operating and controlling module is configured to manipulate at least one of the therapeutic module, the ultrasound imaging module, the optoacoustic imaging module, or the image processing module.

In another embodiment of the present invention, there is provided a (a) illuminating a tissue with the laser pulses of the optoacoustic imaging module of claim 1 and acquiring optoacoustic signals from the illuminated tissue to generate a first optoacoustic image at human physiological temperature; (b) applying an automatic self-focusing algorithm in the image processing module to determine the temperature dependent speed of sound in a region of interest of a patient's body and obtain the optimal resolution for the first optoacoustic image; (c) turning on the temperature cooling source and allow time for the temperature of ROI to change and create gradient of the spatial distribution of temperature, T(r); (d) applying step (a) at a changed temperature and acquiring a second optoacoustic image; (e) applying step (b) and optimizing resolution of the second OA Image to achieve matching between localization of tissue structures in the first image and the second optoacoustic image; (f) normalizing the second optoacoustic image to the first optoacoustic image by dividing every pixel of the second optoacoustic image intensity to that of corresponding pixel of the first optoacoustic image, and thereby produce a normalized image of the optoacoustic image intensity ratio proportional to temperature ratio; (g) measuring temperature with thermocouples placed in the region of interest along temperature gradient to calibrate the map generated in step (g) in absolute temperature value; (h) repeating steps d) through g) to acquire a sequence of optoacoustic images and display of temperature distribution maps, which undergoes changes in the course of calibration procedure; and (i) recording a calibration curve data from images of spatial distribution of the temperature in the calibration tissues or phantoms that resemble properties of the region of interest in the human body.

In this embodiment in tissue with greatly varying speed of sound, the method may comprise replacing step 9b with speed of sound tomography to generate the map of speed of sound in the region of interest and then to generate the most accurate high resolution optoacoustic image. Also in this embodiment accuracy of absolute calibration of temperature may be increased by expanding the range of temperatures to include two characteristic points of well-known temperature, such as (i) temperature at which Gruneisen parameter becomes zero at 4° C. for water and at −12° C. for blood and the optoacoustic image disappears and (ii) the physiological temperature of a human body about 36.5° C.

In yet another embodiment of the present invention there is provided a method for mapping the temperature of a tissue in the course of a thermal therapy procedure, comprising the steps of (a) illuminating a tissue inside a region of interest of a subject using laser pulses of the optoacoustic imaging module of claim 1, at a wavelength within preferred spectral range and safe optical fluence; (b) measuring an optoacoustic response of the tissue by using the ultrasonic probe; (c) constructing a first optoacoustic image at a physiological temperature inside the subject; (d) applying an automatic self-focusing algorithm for the first optoacoustic image to determine the temperature dependent speed of sound in the region of interest of a subject and achieve an optimal resolution for the first optoacoustic image; (e) creating a spatial distribution for temperature in the subject by performing thermal therapy on said subject; (f) illuminating the tissue in the same region of interest at the second temperature point, in the same position of the subject, using laser pulses at the same preferred laser wavelength and the same optical fluence; (g) constructing a second optoacoustic image at the second temperature; (h) applying the automatic self-focusing algorithm for the second optoacoustic image to determine the temperature dependent speed of sound in the region of interest of a subject and achieve an optimal resolution for the second optoacoustic image at the second temperature; (i) generating a normalized image of the optoacoustic image intensity ratio by dividing every pixel value of the second optoacoustic image to corresponding pixel value on the first optoacoustic image; (j) calibrating the normalized optoacoustic image using a calibration curve; (k) producing a map of temperature distribution on the tissues inside the region of interest of the subject; (l) repeating step f) to step k) generating a map of absolute temperature distribution in real time; (m) using the map of the temperature distribution inside the region of interest of the subject to guide the thermal therapy procedure.

In this embodiment the system may generate coregistered overlaid ultrasound and temperature images, displays the temperature map within anatomical tissue structures in the region of interest and uses real time overlaid images to guide thermal therapy procedure. Also, in this embodiment the absolute measurement of temperature may be conducted within a temperature range that includes two characteristic temperatures, one of which is physiological temperature of about 36.6° C. and the second is the protein denaturation temperature of about 52° C. In addition, blood may be the dominating tissue chromophore and the preferred spectral range of laser wavelengths is about 795 nm to about 805 nm and, as such, the absolute measurement of temperature is conducted within a temperature range that includes two characteristic temperatures, one of which is physiological temperature of about 36.6° C. and the second is the temperature about −10° C. at which blood reaches its maximum density and optoacoustic image intensity flips its polarity. Furthermore, water may be the dominating tissue chromophore and the preferred spectral range of laser wavelengths is from about 1300 nm to about 1305 nm and, as such, the absolute measurement of temperature may be conducted within a temperature range that includes two characteristic temperatures, one of which is physiological temperature of about 36.6° C. and the second is the temperature about 4° C. at which water reaches its maximum density and optoacoustic image intensity flips its polarity.

In this embodiment imaging system may be configured to generate real-time two-dimensional and three-dimensional images of tissues in a patient's body. Particularly, three-dimensional images may be generated by assembling two-dimensional slices though the depth of tissues, said two-dimensional slices are obtained by scanning a hand-held ultrasound probe on the surface of an area of a patient's body. Also in this embodiment the method may provide guidance for cryotherapy based on the phenomenon of change of sign of the optoacoustic signal from positive to negative when temperature in the specified region of interest reaches and surpasses the point of maximum density and zero thermal expansion.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Measurements of Temperature Dependence of Grüneisen Parameter

Optoacoustic (OA) thermography is a promising method for temperature monitoring in hypo- and hyperthermal medical treatment. A basic phenomenon associated with the invented method of temperature measurements is presented in FIG. 1. This method is based on high temperature sensitivity of the Grüneisen parameter. OA signal amplitude $V_{OA}$ can be expressed as: $V_{OA} \propto \Gamma \mu_a F$, where $\Gamma$ is thermoelastic efficiency or Grüneisen parameter of light-absorbing material, $\mu_a$ is optical absorption coefficient, F is local optical fluence. Grüneisen parameter incorporates three components[6]: volumetric thermal expansion ($\beta$), speed of sound for longitudinal waves (V), and specific (per mass) heat capacity at constant pressure ($C_p$): $\Gamma = \beta V^2 / C_p$.

The method is validated using optically absorbing aqueous solutions of nickel and cupric sulfate. Two-dimensional optoacoustic imaging is employed to improve sensitivity and precision by measurements with high signal-to-noise ratio (SNR). The experimental setup is designed for simultaneous studies of multiple samples, which allowed confinement of systematic errors caused by spatial fluctuations of laser fluence and distortions of propagating optoacoustic waves. Optical absorbance of the studied solutions has negligible dependence on temperature. The studied aqueous solutions have thermodynamic properties and Gruneisen parameter, which are different from pure water and are dependent on concentration. The method provides data insensitive to spatial variations of laser fluence and optical absorbance. Therefore, temperature-dependent changes of the Grüneisen parameter can be reliably evaluated by this method. The proposed methodology by estimating temperature dependence of Grüneisen parameter for different concentrations of hexahydrate nickel sulfate in the range of temperatures from 4 to 40° C. is validated. This range is important in future applications of optoacoustic imaging for non-invasive monitoring of tissue hypothermia.

Image intensity of aqueous solution samples was gradually decreasing following the local temperature trend, and eventually became indistinguishable from background. Further cooling resulted in re-appearance and growth of the optoacoustic response from the sample, but now registered as the image with opposite (negative) polarity. FIG. 1 provides the first direct observation of the change in polarity of optoacoustic image. Such a positive-negative transition of optoacoustic intensity is expected from aqueous compounds due to nil volumetric thermal expansion coefficient achieved at the extremum of the compound's density. For example, such an effect is predicted for water with maximum density at 3.98° C. It is provided below an example showing direct experimental evidence that optoacoustic response completely disappears at the temperature of maximum density.

Example 2

Experimental Calibration System

The laboratory calibration procedure is conducted using phantoms. The system comprises the following components: Ti:Sapphire pulsed laser that emits in the preferred range of wavelengths 800-805 nm for a live biological tissue containing blood. This laser also has preferred pulse duration of 5 to 10 ns for maximum efficiency of thermal conditions dependent optoacoustic response of tissue generation in tissue. Optical fiber bundles are used for light delivery to tissue phantom, however other means to deliver light also can be used. Ultrasound probe is used for two purposes: it emits and detects ultrasonic waves in the ultrasound imaging mode, and it also detects optoacoustic signals of thermal conditions dependent optoacoustic response of tissue. The probe is connected to a multichannel electronic system, which amplifies, records and processes signals and transmits the processed signals to a computer, which reconstructs images and also controls the whole system. The electronic system can also be used for at least partial image reconstruction. Thermocouples provide absolute temperature readings for calibration purposes. A thermostat system provides conditions similar to thermal therapy.

In this experiment, Ti-Sapphire output of the laser unit was tuned to 800 nm and produced 6 ns, 16 mJ per pulse laser radiation with pulse repetition rate of 10 Hz. Two optical fiber bundles delivered light to the samples. Rectangular output apertures were 1.5 mm×50 mm each and produced laser fluence about 2 mJ/cm$^2$ at 20 mm depth. The probe and fiberoptic outputs were hermetically sealed to enable operation in liquid environment.

A chest freezer was employed for cooling of a thermostat tank. The temperature was measured and logged by digital thermometer with precision of 0.1° C. The 1.5 L tank was filled with coupling solution and was subject to 0.2° C./min cooling rate. The cooling from 40 to 4° C. took about 3 hours. Simultaneously laser power was registered by pyroelectric energy meter to record potential laser fluence fluctuations caused by long time operation.

Example 3

The Temperature for the Maximum Density of a Sample Solution ($T_0$)

In this set of experiments, a cupric sulfate model is used to elucidate physical meaning of the parameter $T_0$ in temperature dependent optoacoustic response. Normalized optoacoustic intensity and density of aqueous cupric sulfate solutions were measured as a function of temperature. The cupric sulfate was preferred over hemoglobin, since it produces larger variation of $T_0$ for the set of achievable concentrations. To eliminate possible effects of the acoustic coupling medium, experiments were performed using distilled water and sodium chloride (23 wt %). FIG. 3A shows normalized optoacoustic intensity for two concentrations of cupric sulfate and calculated normalized Grüneisen parameter of water as a control. The Grüneisen parameter of water was calculated with 1° C. intervals using temperature dependences of speed of sound, specific heat capacity, and thermal expansion coefficient. FIG. 3B shows $T_0$ directly measured as a temperature at zero optoacoustic intensity and its linear regression as a function of concentration. Data matches previous results obtained by extrapolation of the fitted data. The measurements were not affected by using different surrounding media, implying that the entire optoacoustic stress generation happens inside the tubes with sample solutions. FIG. 3C shows two temperature dependent curves of density. The lower one demonstrates known relationship for water. The top one measured relationship for 240 mM cupric sulfate. Arrows indicate maxima of the fitted parabolic functions. Consistent with the Despretz's law, maximum density for cupric sulfate is shifted towards more negative temperatures. FIG. 3D summarizes measured temperatures of the maximum density for different concentrations of cupric sulfate. When fitted with a linear regression model, the resultant equation effectively matches the one obtained for $T_0$ measured via normalized optoacoustic imaging. The equivalence of two relationships allows one skilled in the art to conclude that $T_0$ represents the temperature of maximum density of a sample solution, which is manifested by the absence of thermal expansion, and therefore optoacoustic response. Note, that the data fits in the FIGS. 3B and 3D intercept the ordinate axis at about 4° C., which corresponds to the temperature of maximum density of the pure solvent, i.e. distilled water.

Example 4

One-Valued Normalization of Temperature-Dependent Optoacoustic Response (ThOR) Independence of the Method on Laser Fluence This experiment demonstrates one-valued normalization of temperature-dependent optoacoustic response (ThOR) at certain temperature caused by existence of zero optoacoustic signal in aqueous solutions. It provides independence of the method on laser fluence.

Median intensity of the optoacoustic image was measured in each pixel of region of interest as a function of temperature for multiple consecutive frames. To evaluate spatial confinement of the laser fluence, samples with the same salt solutions located at different distances (Z) from the light illuminators and US probe are visualized. Tubes filled with 240 mM cupric sulfate solution were placed at the distances of 15 and 25 mm from the probe. Due to optical scattering and laser beam divergence, the laser fluence decreased with depth resulting in reduced optoacoustic intensity for the lower tube (FIG. 4A). Temperature dependences of both samples exhibited linear trend in the temperature range from 4 to 40° C. When normalized optoacoustic image intensity values to those measured at physiologically relevant 37° C., perfectly coinciding straight lines were obtained (FIG. 4B). The fluctuation of laser energy in the course of the experiment was about ±4%, but the averaged results of multiple laser pulses, which render the measurement accurate.

Independence of the Method on Optical Absorption Coefficient

This set of experiments explore one-valued normalization of temperature-dependent optoacoustic response (ThOR) at certain temperature caused by existence of zero OA signal in aqueous solutions, which provides independence of the method the optical absorption coefficient. Direct comparison of temperature functions for OA response from samples with different optical absorbance and equal or almost equal thermodynamic parameters was challenging. Variation of optical absorbance due to salt concentration was unacceptable as it could change thermodynamic properties of the solution as well. Therefore, two different salts—cupric sulfate and nickel sulfate were used. With the same concentrations, the thermodynamic characteristics of the two solutions are expected to be very similar. These compounds have the same anionic group and their cations are close by weight and radius. This is the reason why expected similar thermodynamic behavior of these solutions are expected. At the same molar concentration aqueous solution of cupric and nickel sulfates have one order difference in optical absorption at the wavelength of 800 nm. There are $\varepsilon_{800\ nm}=10.57\pm0.13$ M$^{-1}$ cm$^{-1}$ in CuSO$_4$.5H$_2$O and $\varepsilon_{800\ nm}=0.95\pm0.04$ M$^{-1}$ cm$^{-1}$ in NiSO$_4$.6H$_2$O. The ratio of intensities of OA images for nickel and cupric solutions placed at the same distance from the probe was proportional to the difference in optical absorbance (FIG. 5A). After normalization of OA image intensity to that measured at 37° C., curves in FIG. 5B coincide with each other. Note, that the sample of lower absorbance revealed higher sensitivity to laser energy fluctuations. Experimental evidence of FIGS. 4A-4B and FIGS. 5A-5B indicates that the method allows indirect measurements of the relative temperature changes of the Grüneisen parameter.

Example 5

Correlations Between Thermodynamic Properties and the Grüneisen Parameter

In this experiment, the effects of the thermodynamics properties on the Grüneisen parameter are explored. The datasets from nickel sulfate solutions at different concentrations were plotted on the same graph (FIG. 6A). The plots have different linear slopes due to different concentration of $NiSO_4$ salt. Their zero optoacoustic signal temperature decreases with increased concentration of salt (FIG. 6A). The graphs indicate that the temperature of zero optoacoustic signal can be considered an important physical parameter of a particular solution. On the other hand, through thermal conditions dependent optoacoustic response measurements in tubes filled with nickel sulfate solution placed various optoacoustic coupling media, it is proved that the parameter $T_0$ is independent on optoacoustic coupling medium that surrounded the tubes (FIG. 6B). FIG. 6B presents the results for the experiments with deionized water and aqueous solutions of ethanol (40 v/v %) and sodium chloride (23 wt %) as different coupling liquids. Similar to deionized-water, NaCl solution is characterized by its speed of sound increasing with temperature. In the contrast, the ethanol solution has its speed of sound reducing with temperature. Change of the surrounding solution requires corresponding adjustment of speed of sound during the optoacoustic image reconstruction, but the temperature dependence of optoacoustic image intensity is not affected. Concentration dependence of $T_0$ is still linear and agrees well with the results for deionized water as an optoacoustic coupling medium.

Example 6

Accuracy of Processing Thermal Conditions Dependent Optoacoustic Response Data

The normalized Thermal Conditions Dependent Optoacoustic Response ThOR) data was fitted with a second order polynomial function consistent with the prior art. According to the experimental methodology, the function is expressed by in the following equation:

$$\overline{OA} = -\frac{4\Delta T_{max}}{(T_1 - T_0)^2}(T - T_0)(T - T_1) + \frac{T - T_0}{T_1 - T_0};$$

where is the normalized optoacoustic intensity; T—temperature (° C.), $T_1$—fixed normalization temperature, where. In biological applications, it is prudent to select $T_1$ as a normal physiological temperature, for humans $T_1=37°$ C.; $T_0$ is the temperature of zero optoacoustic response; $\Delta T_{max}$ is a maximum nonlinear temperature deviation in the temperature range $[T_0\ T_1]$. If $\Delta T_{max}=0$, the function becomes linear, identical to the one described in previous studies of the aqueous cupric sulfate in the smaller temperature range. FIG. 7 helps to understand the mathematical meaning of $\Delta T_{max}$. Temperature dependent behavior of the normalized optoacoustic response can be represented as a sum of its linear and nonlinear components. The linear component connects the points $(T_0, 0)$ and $(T_1, 1)$ with a straight line:

$$\overline{OA}_L = \frac{T - T_0}{T_1 - T_0}.$$

The nonlinear component is represented by the parabolic portion:

$$\overline{OA}_{NL} = -\frac{4\Delta T_{max}}{(T_1 - T_0)^2}(T - T_0)(T - T_1).$$

Nonlinear temperature deviation $\Delta T=T-T^*$ could be calculated by assuming $$\overline{OA}_{NL}(T) = \overline{OA}_L(T^*):$$

$$\Delta T(T) = -\frac{4\Delta T_{max}}{(T_1 - T_0)^2}(T - T_0)(T - T_1).$$

with maximum $\Delta T_{max}$ at $T=(T_0-T_1)/2$.

The procedure to find the parameters $T_0$ and $\Delta T_{max}$ for each sample was as following:

(i) $T_0$ was estimated directly for each sample as a temperature where polarity of the normalized optoacoustic intensity changed from positive to negative. Due to very small noise, zero transition of the normalized optoacoustic intensity is determined with accuracy limited by individual temperature measurements.

(ii) Not-normalized optoacoustic intensity data was fitted with a parabolic function, with fixed parameters $T_0$ and $T_1$, and unknown $\Delta T_{max}$ and the normalization scaling factor.

Example 7

Red Blood Cells as a Universal Optoacoustic Sensor

In live organisms, the hemoglobin, which under normal physiological conditions is exclusively compartmentalized inside red blood cells (RBCs), is the only chemical tissue component with significant optical absorption at 805 nm, which was also reported to be independent of oxygenation status and temperature. The intracellular concentration of hemoglobin is a part of broad homeostasis and is relatively constant for individual species. For example, for adult humans it varies in the range 330-360 mg/ml or 5.1-5.6 mM. Therefore, it is expected that despite significant spatial variations of hemoglobin concentrations caused by hematocrit differences between major blood vessels and capillaries and tissue-specific density of vascularization, in vivo optoacoustic response at 805 nm will be defined by physical properties of intracellular hemoglobin. It is showed in FIG. 8 that the intensity-normalized 2D optoacoustic imaging could be reliably used for remote temperature monitoring inside optically absorbing solutions, if a solution- and concentration-specific parameter $T_0$ is known. The material parameter $T_0$ was extracted from linear fit of the measured data as a temperature at zero optoacoustic response. The implemented normalization of the optoacoustic image intensity at initial temperature provided spatial confinement of optical fluence and absorption, which is necessary for potential in vivo applications. Here the same imaging approach is used to study temperature dependent behavior of optoacoustic response in whole and diluted porcine blood contained inside ultrathin-wall plastic tubes. Blood dilution was implemented in order to simulate conditions of physiological variability of hematocrit across systemic vasculature and capillary networks. Phosphate buffered saline (PBS, pH 7.4) was used to dilute the whole blood while preserving the integrity of red blood cells. Optoacoustic imaging was performed while slowly decreasing the temperature from +37 to −15° C. Aqueous solution of sodium chloride at concentration of its eutectic point (23 wt %) with freezing temperature at about −21° C. was used as an acoustically coupling medium. FIG. 8B shows optoacoustic response from diluted blood samples simulating physiological range of hematocrit across the entire vasculature (from systemic blood vessels down to capillaries, FIG. 8A. While dilution of blood samples resulted in proportional decrease of the optoacoustic intensity measured at a particular temperature, the entire data ensemble still intersected in the same point of zero optoacoustic response at $T_0=-13.1\pm0.3°$ C. (N=4). Here and anywhere else below, if not explicitly stated, statistical data is presented as average±standard deviation with number of samples indicated in parenthesis. After normalization at physiological 37° C. the graphs merge into a universal calibration curve (FIG. 8C), which can be accurately approximated by a second order polynomial. The second order approximation is consistent with thermal behavior of Grüneisen parameter for water and optoacoustic response measured from in vitro retina tissue and turkey breast in a wide range of temperatures. Data from whole blood samples obtained from eight animals were analyzed and the temperature of zero optoacoustic response for the porcine blood was estimated as $T_0=-12.8\pm0.5°$ C. It is found that the thermal expansion coefficient of erythrocyte's cytoplasm is the factor dominating in the observed temperature-dependent optoacoustic response of blood samples. The functional trend and the measured temperature of zero optoacoustic response are in agreement with those of thermal expansion coefficient estimated for erythrocyte concentrates in the temperature range from 4 to 48° C. However, $T_0$ extrapolated from the data reported on plasma ultrafiltrate is much higher, and is rather close to the one measured in pure PBS.

To prove that the universal temperature dependent optoacoustic response observed in blood is confined within the stable internal environment of erythrocytes, a control imaging of hemoglobin solutions is performed (FIG. 9A-9B). The hemoglobin powder was dissolved in PBS to keep physical and chemical properties of hemoglobin within physiological range. The solutions were prepared at different concentrations from highly diluted 12 mg/ml or 0.186 mM to the concentration mimicking whole blood at average hematocrit (120 mg/ml or 1.860 mM). As presented in FIG. 9A, all normalized optoacoustic imaging intensities for different Hb concentrations including the one that matches whole blood, cross the zero intensity line at temperatures substantially different from that of whole blood with intact red blood cells (FIG. 9A). It was found that in contrast to blood, there is a linear decrease of temperature $T_0$ (at which one can observe zero value of ThOR) with hemoglobin concentration from about +3° C. at low concentrations to about −3° C. for 1.86 mM solutions (FIG. 9B).

Example 8

Normalized Optoacoustic Image Intensity as a Function of Temperature

FIG. 10A shows normalized OA image intensity as a function of temperature for two groups of blood (4 subjects in each group) representing male and female blood. One again it is verified that the system of the present invention performs well giving accurate measurements in male and female blood, being independent on the fact that the samples differ in their hematocrit and associated optical absorption coefficients.

FIG. 10B demonstrates the effects of optically scattering compared to clear media. The transparent surrounding was replaced by scattering medium to study behavior of thermal conditions dependent optoacoustic response for blood in conditions closed to a potential medical application. For this purpose, fat free milk was employed as a coupling liquid. The experiment was performed at the temperature range from 30 to 5° C. to avoid milk freezing. The curves of temperature dependence for optoacoustic image intensity in scattering medium replicate the previous result in transparent medium (FIG. 10B). Thus, it is revealed that whole and diluted blood has the same thermal conditions dependent optoacoustic response. The integrity of erythrocytes during performed experiments was confirmed. The found phenomenon was observed in both, transparent and scattering media.

Example 9

The Temperature Calibration Curve

The temperature calibration curve is made from individual thermal conditions dependent optoacoustic response (ThOR) and normalized optoacoustic imaging intensity. FIG. 11A shows sample-to-sample variation of ThOR magnitude as a function of temperature variations. Depending on the temperature range, the accuracy varied from ±2.3° C. to ±0.4° C. The accuracy averaged over the entire temperature range was about ±1.3° C. A dramatic improvement in the accuracy of temperature measurement was achieved with measurements of the normalized optoacoustic image intensity. The error of measuring image intensity in each pixel is at least an order of magnitude higher than that of each sample of optoacoustic signals, i.e. ThOR magnitude, because many optoacoustic signal samples contribute to one image pixel. FIG. 11B shows that the accuracy of temperature measurement from the two-dimensional map of the temperature distribution, i.e. the accuracy the method can achieve is about 0.1° C.

Example 10

Temperature Mapping

Temperature mapping was conducted using tissue-mimicking optoacoustic phantom made of optically scattering PVCP background with inserted seven tubes filled with live blood preheated to 36.5° C. FIGS. 12B-12D show 3 sample frames of a movie recorded with video rate. The frames present temperature images of tube cross-sections (circles) changing their intensity converted into color from red (image frame #1, right upper) to yellow (image frame #20, left lower) to blue (image frame #56, right lower) depending on gradually decreasing local temperature mapped using the system of the present invention. A blue square on images represent is a tube filled with cold solution of NaCl at −11° C. circulated in the tube. This video demonstrates that the image guided system can acquire optoacoustic images and normalize them to the first image obtained at the physiological body temperature in real time thereby generating and displaying a temperature map.

Example 11

Clinical Application

FIG. 13 demonstrates clinical application of the invented system for the thermal therapy procedure of prostate cancer cryoablation with optoacoustic temperature monitoring. Ultrasound imaging shows anatomy of region of interest and allows precise insertion of 3 or more cryoablation needles. One thermocouple needle may be used for control. Transrectal ultrasonic probe is designed to include fiberoptic bundles for optical illumination with NIR laser pulses. Deep penetration of NIR light at preferred wavelengths through the scattering medium allows non-invasive temperature monitoring with clinical significance. Mapping of distribution of tissue temperature allows doctors to monitor temperature in multiple pivotal locations, such as rectal wall, nerves and urethra and modify the procedure in real time to avoid side effects of damaged normal tissue.

FIGS. 14A-14D shows clinical images that can be obtained with the invented system. Based on the reported findings, the following procedure for non-invasive monitoring of temperature using 2D optoacoustic imaging at 805 nm laser wavelength were performed: (1) Prior to any thermal intervention record optoacoustic image from the vascularized tissue regions of interest at a normal local physiological temperature, e.g. 37° C.; (2) At any subsequent moment, obtain intensity-normalized optoacoustic response and convert it to the local temperature via the universal blood calibration curve measured for a particular biological population. Since in vivo optoacoustic response is generated predominantly within blood vessels and normalization makes it independent of hematocrit and local fluence, the calibration should remain valid across the entire field of view.

Cryoablation involves rapid localized temperature decrease, and there is a crucial requirement to minimize collateral thermal damage in the innervation areas near rectal wall, which cannot be addressed by direct invasive temperature measurements with the needle probes. On the other hand, two-dimensional optoacoustic imaging of temperature could be implemented in this case using a modified transrectal linear ultrasound probe, which has imaging characteristics similar to the general-purpose clinical probe used in this studies. It was expected that the normalized optoacoustic imaging technique shows better accuracy when monitoring lower temperatures due to non-linearity of the temperature calibration curve, which decreases sensitivity for higher temperatures (FIG. 7). Full applicable range of temperatures measured in blood is constrained by thermal stability of hemoglobin within red blood cells to preserve intact near-infrared spectral properties. Another critical requirement of the technique is hemoglobin compartmentalization inside erythrocytes. Blood samples that underwent the cooling procedure down to −15° C. were examined under 40× light microscope with additional digital zoom and did not observe any morphological changes in red blood cells, which indirectly confirms that the hemoglobin compartmentalization was maintained during the experiments. However, cryoablation is known to produce disruptive effects within cell membranes, caused by repetitive cycles of fast freezing followed by slow thawing, an indication that the rate of temperature change could be another important factor to consider in development of the optoacoustic temperature mapping technology.

Tissue thermal coagulation that occurs at about 52° C. represents a limitation of the method on the other end of the temperature curve. Statistical variance of $T_0$ is another important characteristic that will affect accuracy of the technique and should be estimated for the entire clinical population. So far, according to the experimental results, subject-to-subject variations in $T_0$ that could be caused by differences in cytoplasmic composition including hemoglobin concentration inside red blood cells are not substantial. $T_0$ of blood samples from 8 animals were measured with standard deviation of 0.5° C. Depending on the clinical application the variance of the $T_0$ could be further minimized by categorizing subjects based on sex, age, etc. Prior to performing clinical procedures of image guided thermal therapy procedures with temperature mapping, one needs to take into account potentially changing hemostasis of blood vessels, which can effect accuracy of the optoacoustic temperature measurements in vivo. Therefore, a coefficient can be introduced into the calibration curve to account for gradually changing blood flow and hemostasis.

While the present invention is described with reference to one or more particular 15 embodiments, those skilled in the art will recognize that many changes may be made thereto without departing from the spirit and scope of the present invention. Each of these embodiments and obvious variations thereof is contemplated as falling within the spirit and scope of the claimed invention set forth in the following claims.

The following references are cited herein.

1. A. A. Oraevsky and S. L. Jacques, R. O. Esenaliev, U.S. Pat. No. 5,840,023
2. Esenaliev et al., U.S. Pat. No. 6,309,352
3. Esenaliev et al., Proceedings SPIE 3601:268-275 (1999).
4. Shah et al., Journal of Biomedical Optics 13:034024 (2008).
5. Pramanik, M. and Wang, L. V., Journal of Biomedical Optics 14:054024 (2009).
6. Nikitin et al., Journal of Biomedical Optics 17:061214 (2012).
7. Yao, J et al., patent application U.S. Ser. No. 13/190,334, Jul. 23, 2010.
9. Petrova et al., A., Optics Express 25077-25090 (2013).
10. N. Bilaniuk and G. S. K. Wong, J. Acoust. Soc. Am. 93:1609-1612 (1993).
11. Zhmakin A. I., "Fundamentals of Cryobiology: Physical Phenomena and Mathematical Models", Springer, 2010, pp. 278.
12. Pennes H. H. J. Appl. Physiol. 1:93-122 (199).
13. Kolios et al., *Phys. Med. Biol.* 40:477-494 (1995).
14. Rivens et al., *Int. J. Hyperthermia* 23(2):121-39 (2007).
15. Saccomandi et al., *Int. J. Hyperthermia* 29(7):609-19 (2013).
16. C. D. Arvanitis and N. McDannold, *Med. Phys.* 40(11): 112901 (2013).
17. Ke et al., *J. Biomed. Opt.* 19(2):26003 (2014).
18. Shah et al., *J. Biomed. Opt.* 13(3):034024 (2008).
19. Yao et al., *Opt. Lett.* 38(24):5228-31 (2013).
20. Chen et al., *J. Biophotonics* 6(6-7):534-42 (2013).
21. Nikitin et al, *J. Biomed. Opt.* 17(6):061214 (2012).
22. Petrova et al., *Opt. Express* 21(21):25077-25090 (2013).
23. Yao et al., *J. Biomed. Opt.* 19(1):17007 (2014).
24. Esenaliev et al., *Proc. SPIE* 3601:268-275 (1999).
25. Larin et al., *J. Phys. D* 38(15):2645-2653 (2005).
26. Petrova et al., *Proc. SPIE* 8943:89430S (2014).
27. M. Pramanik and L. V. Wang, *J. Biomed. Opt.* 14(5): 054024 (2009).
28. Gao et al., *J. Biomed. Opt.* 18(2):26003 (2013).
29. Gao et al., *Appl. Phys. Lett.* 102(19):193705 (2013).
30. Brinkmann et al., *J. Biomed. Opt.* 17(6):061219 (2012).
31. Roggan et al., *J. Biomed. Opt.* 4(1):36-46 (1999).

32. Cordone et al., *Biophys. Chem.* 24(3):259-275 (1986).
33. Steinke and A. P. Shepherd, *Clin. Chem.* 38(7):1360-1364 (1992).
34. Brix et al., *Radiology* 210(1):269-76 (1999).
35. Chen et al., Small 8:47 (2012).

What is claimed is:

1. An imaging system for visualization and accurate mapping of temperature distribution in absolute values in the region of interest and anatomical structures of live human or animal tissue independently on spatial distribution of the optical fluence in the body and independently on spatial distribution of the tissue optical properties, comprising:
    an optoacoustic imaging module that uses pulsed optical illumination at a preferred wavelength about 795 nm to about 805 nm or about 1300 nm to about 1305 nm;
    an ultrasound imaging module having an ultrasonic probe communicably connected to an electronics system that also serves as a probe and to an electronics system for the optoacoustic imaging module and is configured to emit and to detect ultrasonic waves in an ultrasound imaging mode and to detect optoacoustic signals of thermal conditions dependent optoacoustic response of tissue in an optoacoustic imaging mode;
    an image processing and calibration module connected to the optoacoustic imaging module and to the ultrasound imaging module and configured to generate an image co-registered in space and time from an image generated of the temperature distribution and an image generated of the anatomical structures of the live human or animal tissues;
    an image display module configured to display the co-registered image;
    a therapeutic module configured to apply a thermal treatment to the live human or animal tissue and to monitor and guide thermal therapy procedures therewithin; and
    an operating and controlling module electronically connected with said image processing module and configured to control and manipulate at least one of the modules of the imaging system.

2. The imaging system of claim 1, wherein the optoacoustic imaging module integrates a pulsed laser connected with an imaging module through a light delivery subsystem configured to deliver the laser pulses to the region of interest.

3. The imaging system of claim 1, wherein said image processing and calibration module of the imaging system comprises:
    a calculation module configured to calculate the location and temperature within specific anatomical tissue structures based on the information received in the processing module;
    an image constructing module that generate images based on the calculation from the calculation module and the signals received in the processing module; and
    an user interface communicably connected to said calculation module and said image constructing module.

4. A user-implemented method for calibrating a temperature-structure imaging system, comprising:
    (a) illuminating a tissue with the pulsed optical illumination of the optoacoustic imaging module of claim 1 and acquiring optoacoustic signals from the illuminated tissue to generate a first optoacoustic image at human physiological temperature;
    (b) applying an automatic self-focusing algorithm in the image processing and calibration module to determine the temperature dependent speed of sound in a region of interest of a patient's body and obtain the optimal resolution for the first optoacoustic image;
    (c) turning on a temperature cooling source and allowing time for the temperature of the region of interest to change and to create a temperature gradient of the spatial distribution of temperature, T(r);
    (d) applying step (a) at a changed temperature and acquiring a second optoacoustic image;
    (e) applying step (b) and optimizing resolution of the second optoacoustic image to achieve matching between localization of tissue structures in the first optoacoustic image and the second optoacoustic image;
    (f) normalizing the second optoacoustic image to the first optoacoustic image by dividing every pixel of the second optoacoustic image intensity to that of a corresponding pixel of the first optoacoustic image, and thereby producing a normalized image of the optoacoustic image intensity ratio proportional to temperature ratio;
    (g) measuring temperature within a range of temperatures that include a temperature of zero optoacoustic response and the physiological temperature of a human body with thermocouples placed in the region of interest along the temperature gradient to calibrate the map generated in step (g) in absolute temperature value, said temperature range enabling an increase in accuracy of absolute calibration of temperature;
    (h) repeating steps d) through g) to acquire a sequence of optoacoustic images and a display of temperature distribution maps, which undergo changes in the course of calibration procedure; and
    (i) recording calibration curve data from images of spatial distribution of the temperature in the calibration tissues or in phantoms that resemble properties of the region of interest in the human body.

5. The calibration method of claim 4, wherein, the method comprises replacing step 9b with speed of sound tomography to generate the map of speed of sound in the region of interest and then to generate the most accurate high resolution optoacoustic image.

6. The calibration method of claim 4, wherein the temperature of zero optoacoustic response is the temperature at which Gruneisen parameter becomes zero at 4° C. for water and at −12° C. for blood and the optoacoustic image disappears and the physiological temperature of a human body is about 36.5° C.

7. A method for mapping the temperature of a tissue in the course of a thermal therapy procedure, comprising the steps of:
    (a) illuminating a tissue inside a region of interest of a subject using the pulsed optical illumination of the optoacoustic imaging module of claim 1, at a wavelength within preferred spectral range and safe optical fluence;
    (b) measuring an optoacoustic response of the tissue by using the ultrasonic probe;
    (c) constructing a first optoacoustic image at a physiological temperature inside said subject;
    (d) applying an automatic self-focusing algorithm for the first optoacoustic image to determine the temperature dependent speed of sound in the region of interest of a subject and achieve an optimal resolution for the first optoacoustic image;
    (e) creating a spatial distribution for temperature in the subject by performing thermal therapy on said subject;
    (f) illuminating the tissue in the same region of interest at the second temperature point, in the same position of the subject, using laser pulses at the same preferred laser wavelength and the same optical fluence;

(g) constructing a second optoacoustic image at the second temperature;

(h) applying the automatic self-focusing algorithm for the second optoacoustic image to determine the temperature dependent speed of sound in the region of interest of a subject and achieve an optimal resolution for the second optoacoustic image at the second temperature;

(i) generating a normalized image of the optoacoustic image intensity ratio by dividing every pixel value of the second optoacoustic image to corresponding pixel value on the first optoacoustic image;

(j) calibrating the normalized optoacoustic image using a calibration curve;

(k) producing a map of temperature distribution on the tissues inside the region of interest of the subject;

(l) repeating step f) to step k) generating a map of absolute temperature distribution in real time;

(m) using the map of the temperature distribution inside the region of interest of the subject to guide the thermal therapy procedure.

8. The method of claim 7, further comprising generating coregistered overlaid ultrasound and temperature distribution images, displaying the temperature map within anatomical tissue structures in the region of interest and guiding the thermal therapy procedure based on the real time overlaid images.

9. The method of claim 7, wherein blood is the dominating tissue chromophore and the preferred spectral range of laser wavelengths is about 795 nm to about 805 nm.

10. The method of claim 9, wherein the absolute measurement of temperature is conducted within a temperature range that includes two characteristic temperatures, one of which is a physiological temperature of about 36.6° C. and the second is the temperature about −10° C. at which blood reaches its maximum density and optoacoustic image intensity flips its polarity.

11. The method of claim 7, wherein water is the dominating tissue chromophore and the preferred spectral range of laser wavelengths is from about 1300 nm to about 1305 nm.

12. The method of claim 11, wherein the absolute measurement of temperature is conducted within a temperature range that includes two characteristic temperatures, one of which is a physiological temperature of about 36.6° C. and the second is the temperature about 4° C. at which water reaches its maximum density and optoacoustic image intensity flips its polarity.

13. The method of claim 7, wherein the absolute measurement of temperature is conducted within a temperature range that includes two characteristic temperatures, one of which is a physiological temperature of about 36.6° C. and the second is a protein denaturation temperature of about 52° C.

14. The method of claim 8, wherein said ultrasound and temperature distribution images are real-time two-dimensional and three-dimensional images of tissues in the subject.

15. The method of claim 14, wherein said three-dimensional images are generated by assembling two-dimensional slices though the depth of tissues, said two-dimensional slices are obtained by scanning a hand-held ultrasound probe on the surface of an area of a patient's body.

16. The method of claim 7, wherein the method provides guidance for cryotherapy based on the phenomenon of change of sign of the optoacoustic signal from positive to negative when temperature in the specified region of interest reaches and surpasses the point of maximum density and zero thermal expansion.

* * * * *